(12) United States Patent
Boddy et al.

(10) Patent No.: US 8,709,781 B2
(45) Date of Patent: Apr. 29, 2014

(54) SYSTEM AND METHOD FOR THE HETEROLOGOUS EXPRESSION OF POLYKETIDE SYNTHASE GENE CLUSTERS

(75) Inventors: Christopher N. Boddy, Ottawa (CA); Anthony Garza, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 477 days.

(21) Appl. No.: 12/565,314

(22) Filed: Sep. 23, 2009

(65) Prior Publication Data
US 2010/0184038 A1 Jul. 22, 2010

Related U.S. Application Data

(60) Provisional application No. 61/143,547, filed on Jan. 9, 2009.

(51) Int. Cl.
*C12N 1/21* (2006.01)
*C12N 15/09* (2006.01)

(52) U.S. Cl.
USPC ....................................... 435/252.3; 435/69.1

(58) Field of Classification Search
None
See application file for complete search history.

(56) References Cited

PUBLICATIONS

Letouvet-Pawlak et al., J. Gen. Microbiol., 139, 3243-3252, 1993.*
Rhodes et al., Biochemical Society Transactions, 12:586-587, 1984.*
Winstanley et al., Appl. and Environ. Microl. and Biotechnol., 57, 7, 1905-1913, 1991.*
Menzella et al., J. Indust. Microbiol. and Biotechnol., 33, 1, 22-28, 2006.*
Imaishi et al., J. Bacteriol., 175, 5,: 1550, 1993.*
Alarcon-Chaidez, F.J. et al. RpoN(o54) is required for plasmid-encoded coronatine biosynthesis in *Pseudomonas syringae*. Plasmid, 2003, vol. 49, pp. 106-117.
Rappas, M., et al. Bacterial enhancer-binding proteins: unlocking o54-dependent gene transcription. Current Opinion in Structural Biology, 2007, vol. 17, pp. 110-116.
Sarniguet, A. et al., The sigma factor o s affects antibiotic production and biological control activity of *Pseudomonas fluorescens* Pf-5. Proc. Natl. Acad. Sci., 1995, vol. 92, pp. 12255-12259.

* cited by examiner

*Primary Examiner* — Nancy T Vogel
(74) *Attorney, Agent, or Firm* — George R. McGuire; Frederick J.M. Price; Bond Schoeneck & King, PLLC

(57) ABSTRACT

A system and method for heterologous expression of polyketide biosynthetic pathways from streptomycetes hosts in *Escherichia coli* for the production and discovery of secondary metabolites. Genomic DNA from *Streptomyces rimosus* encoding the oxytetracycline biosynthetic pathway is inserted into the genome of the surrogate host *Myxococcus xanthus*. The *M. xanthus* transcriptional machinery recognizes and uses the streptomycetes promoter regions to express the biosynthetic enzymes. Co-expression in *E. coli* of *S. rimosus* oxytetracycline biosynthesis enzymes and *M. xanthus* $\sigma^{54}$, a key piece of the *M. xanthus* transcriptional machinery, enables *E. coli* to recognize and use the promoters from the *S. rimosus* oxytetracycline biosynthetic pathway, facilitating production of oxytetracycline.

6 Claims, 9 Drawing Sheets

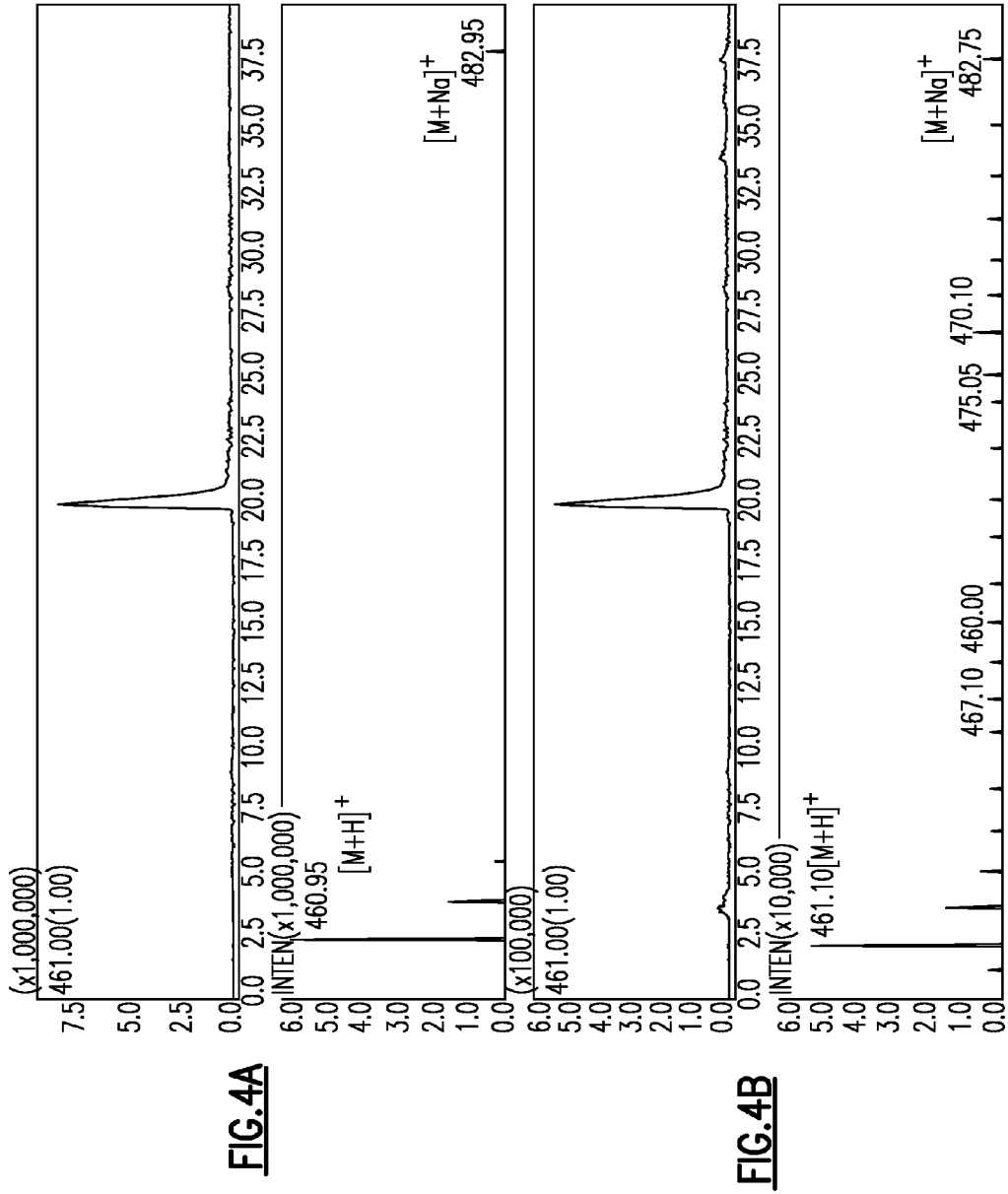

SYSTEM AND METHOD FOR THE HETEROLOGOUS EXPRESSION OF POLYKETIDE SYNTHASE GENE CLUSTERS

CROSS-REFERENCE TO RELATED APPLICATIONS

The present application claims priority to U.S. Provisional Application No. 61/143,547, filed Jan. 9, 2009.

BACKGROUND OF THE INVENTION

1. Field of Invention

The present invention relates to polyketide synthase and, more specifically, to a system and method for the heterologous expression of polyketide synthase gene clusters.

2. Background of Art

Natural products have been a major source of new drugs in all therapeutic areas. In some therapeutic areas, such as antibacterial and anti-cancer agents, greater than 70 percent of drugs approved between 1981 and 2002 have been derived from or inspired by natural products. In addition natural products serve as tools to better understand drug targets and pathways in human disease. By interacting with novel targets, natural products validate these targets for drug discovery, enabling diversification of the pharmacopoeia.

Bacterially derived polyketides and non-ribosomal peptides have played an extremely important role in natural product based drug discovery, particularly in the areas of antibiotic and anticancer agents. For example, one of the most recently approved anticancer agents, ixabepilone, is derived from the mixed polyketide non-ribosomal peptide epothilone B. In addition to antibiotic and anticancer activities, polyketides and non-ribosomal peptides have been shown to possess bioactivity in all major therapeutic areas.

Bacterial natural products, including polyketides and non-ribosomal peptides, offer key advantages in identifying biologically active small molecules. Because these compounds have evolved to offer their hosts increased fitness over other competing organisms, natural products have been pre-selected to target biological systems. As a direct result, natural products generally have appropriate solubility and stability in biologically relevant environments such as serum and cytoplasm and are often able to cross biologically relevant membranes. Natural products have been shown to offer unmatched chemical diversity and structural complexity as compared to de novo small synthetic molecules. It has been estimated that natural products libraries will have approximately a two orders of magnitude greater "hit rate" in identifying lead compounds than synthetic compound libraries.

Isolation of new bioactive polyketides for drug discovery and production of known polyketides for drug development is often limited, however, by the ability of the producing organisms to generate sufficient quantities of the desired compound. In addition, the traditional natural product screening approach used for the development of therapeutics has serious, inherent limitations, including building and maintaining high-quality natural product libraries, the frequent rediscovery of known compounds during the screening process, and difficulties associated with obtaining sufficient amounts of potential lead compounds for further evaluation. Despite the proven track record and intrinsic advantages of natural products in drug discovery, the majority of pharmaceutical companies downgraded or terminated their natural product research programs over the last twenty years. A driving force in this change was the difficulties associated with building and maintaining high quality natural product libraries. Isolation of natural products, which are normally trace components, from producing organisms is a challenging task and generally produces small quantities of compound. In addition the natural sources often cannot provide sufficient material for clinical develop of lead compound due to the limited sustainability of harvesting the producing organism. By the late 1980s, the natural products isolated were often known compounds leading to high rates of rediscovery. Rediscovery severely limited the accessible diversity of natural product libraries.

The inherent diversity of bacterially derived polyketide and non-ribosomal peptide natural products has not yet been tapped. Over one million bacterial strains have been cultured and screened for bioactive metabolites, leading to hundreds of clinically approved drugs and thousands of bioactive compounds. This represents less than 1 percent of the potential diversity available from bacterial sources. Genome sequencing has demonstrated that bacterial species generally posses gene clusters encoding for approximately twenty biosynthetic pathways. For culturable organisms traditional screening approaches have yielded two to three metabolites per species. Extrapolation from these data suggest that there are coding sequences for upwards of 200,000 natural products present in a single soil sample and that current screening approaches only access 200 to 500 compounds. Tapping this enormous natural product diversity will require a culture independent approach to compound screening.

Due to their important pharmaceutical role, methods for efficient production of polyketides are also highly desired. New methods for the discovery of cryptic or silent polyketides from biological pathways that are present yet not expressed have also increased interest in drug discovery. Complexities in the structure and stereochemistry of polyketides, however, limit synthetic production methods and have increased interest in microbial fermentation. Microbial fermentation as a means of production of polyketides has become a prominent economical method, but 99.8% of microbes available in native environments are not readily culturable or produce unacceptably low amounts of polyketides. The heterologous expression of secondary metabolites in more amenable heterologous hosts has recently become an attractive method for the production of polyketides. This approach has been used in the production of epothilone D for anticancer clinical trials. Heterologous expression of polyketide biosynthetic pathways proves difficult due to the complexity of the enzymatic pathways and the need for simultaneous expression of all genes in the pathway. These obstacles have prevented the expression of polyketides from poor fermentation hosts in the fermentation workhorse, *Escherichia coli*.

Polyketides are biosynthesized by complex pathways containing multiple polyketide synthases, tailoring enzymes, and enzymes mediating resistance to the polyketide product. Oxytetracycline, as seen in FIG. 1B, which is produced by *S. rimosus*, provides an archetypical example of an aromatic polyketide synthase biosynthetic pathway. The backbone of oxytetracycline is assembled from a minimal PKS consisting of four proteins a ketosynthase (KS), a chain length factor (CLF), an acyl transferase (AT), and an acyl carrier protein (ACP), as seen in FIG. 1A. The minimal PKS catalyses repetitive Claisen-like condensations using ten sequential units of malonyl-CoA. Following backbone production, a minimum of six tailoring enzymes complete oxytetracycline biosynthesis. Overall the biosynthesis of oxytetracycline requires over a dozen enzymes working in concert.

The heterologous expression of biosynthetic pathways, such as the oxytetracycline biosynthetic pathway, require the heterologous host to recognize the promoters upstream of the biosynthetic genes and express the proteins. Both myxobacteria and streptomycetes have demonstrated an ability to recognize a broad range of promoters as displayed by their ability to produce an enormous number of polyketide products 4. Myxobacteria are the third largest producers of secondary metabolites behind actinomycetes and bacilli. Heterologous expression of a myxobacterial secondary metabolite has been observed in a streptomycetes host providing evidence for streptomycetes transcriptional machinery's ability to recognize and use myxobacterial promoter regions. However expression of a secondary metabolite from a streptomycetes has not been observed in a myxobacterium host.

Two approaches have been used to ensure expression of a biosynthetic pathway in a heterologous host, however both are limited in their scope and applicability. The first approach involves the selection of a host strain highly related to the native strain. By using highly related strains, the transcriptional machinery is expected to be conserved and therefore able to transcribe the heterologous genes. This approach has proven successful for the heterologous expression of polyketide gene clusters from the genus *streptomyces*. However, it is limited to producing polyacetate-derived polyketides. Additionally when gDNA from unrelated organisms are used the *streptomyces*-based heterolgous expression system fails to generate useful quantities of product. This approach is thus not expected to perform well for heterologous expression of pathways from diverse organisms, such as unculturable bacteria.

A second approach to ensuring heterologous expression is to replace the native promoters in a biosynthetic pathway with promoters known to function in the host strain. Both polyketide and non-ribosomal peptides have been expressed under the control of the T7 promoter in *Escherichia coli*. This approach is not well suited to screening large libraries of unsequenced gDNA as it is extremely labor intensive and requires foreknowledge of the genes in the biosynthetic pathway.

SUMMARY OF THE INVENTION

It is a principal object and advantage of the present invention to provide a system and method for generating sufficient quantities of polyketides for identification.

It is a principal object and advantage of the present invention to provide a system and method for generating sufficient quantities of polyketides for determining pharmaceutical benefits.

It is an additional object and advantage of the present invention to provide a system and method for the heterologous production of polyketides for commercial applications.

It is a further object and advantage of the present invention to provide a system and method for the efficient production of polyketides for commercial applications.

Other objects and advantages of the present invention will in part be obvious, and in part appear hereinafter.

The present invention comprises a mechanism for heterologous expression of polyketide biosynthetic pathways in host organism thereby providing a new mechanism for the production and discovery of secondary metabolites. In particular, the present invention takes advantage of the discovery that, contrary to conventional belief, the $\sigma^{54}$ factor is highly conserved and responsible for regulating transcription for a diverse variety of non-essential functions in bacterial cells. The present invention therefore provides a system and method for producing polyketides and non-ribosomal peptides using the $\sigma^{54}$ transcription system.

As an example of a method of producing polyketides from a host using the $\sigma^{54}$ system, genomic DNA from *Streptomyces rimosus* encoding for the oxytetracycline biosynthetic pathway was inserted into the genome of the surrogate host *Myxococcus xanthus*. Successful production of oxytetracycline verifies the ability of the *M. xanthus* transcriptional machinery to recognize and use streptomycetes promoter regions. *E. coli* containing the *S. rimosus* oxytetracycline gene cluster is unable to produce oxytetracycline due to the inability of the *E. coli* transcriptional machinery to recognize streptomycetes promoter regions. Co-expression in *E. coli* of *M. xanthus* $\sigma^{54}$, a key piece of the *M. xanthus* transcriptional machinery, enables *E. coli* to recognize and use the promoters from the *S. rimosus* oxytetracycline biosynthetic pathway, facilitating production of oxytetracycline.

Both myxobacteria and streptomycetes possess GC rich sigma factors involved with gene expression. The transcriptional machinery of *Myxococcus xanthus* uses the GC rich alternative sigma factor $\sigma^{54}$ encoded by the rpoN gene. Due to similarities in GC content and the presence of similar $\sigma^{54}$ transcriptional machinery, *M. xanthus* is an ideal host for the production of oxytetracycline. The $\sigma^{54}$ transcriptional machinery from *M. xanthus* is responsible for the recognition of the promoter regions of the oxytetracycline biosynthetic pathway. Production of oxytetracycline in *M. xanthus* confirms its ability to recognize $\sigma^{54}$ promoter regions and also allow the first production of a streptomycetes secondary metabolite from a myxobacterium. Heterologous expression in *Escherichia coli* would not be expected due to the distinct differences in GC content when compared to *S. rimosus* and the lack of similar (J54 transcriptional machinery. The $\sigma^{54}$ of *E. coli* is distinctly AT rich and the major sigma factor, $\sigma^{70\circ}$ in *E. coli*, has little sequence similarity to $\sigma^{54}$. The co-expression of transcriptional machinery from *M. xanthus* with the oxytetracycline biosynthetic pathway from *S. rimosus* enable *E. coli* to recognize and express the oxytetracycline biosynthetic pathway, producing oxytetracycline.

The present invention is not limited to the product of oxytetracycline and may be adapted to produce both unknown and known polyketides and non-ribosomal peptides as the present invention relates to the general mechanism for producing such secondary metabolites. In particular, the use of the PromScan bioinformatics tool (http://molbiol-tools.ca/promscan/) has revealed that the degree of $\sigma^{54}$ promoter conservation among diverse bacterial species is very high (Barrios et al., 1999) and $\sigma^{54}$ promoter sequences differ greatly from those of their $\sigma^{70}$ type promoter counterparts, it is relatively easy to identify potential $\sigma^{54}$ promoters from genome sequences or other DNA sequencing information. Trial runs with known *M. xanthus* promoters ($\sigma^{54}$ promoters and non-$\sigma^{54}$ promoters) correctly identified the $\sigma^{54}$ promoter elements. Trial runs have been performed in several other bacterial species with similar results. In addition, studies using DNA microarray expression data and bioinformatics tools identified potential $\sigma^{54}$ promoter targets of 6 *M. xanthus* EBPs. Subsequent gel shift assays showed at least 1 EBP bound to each of the potential $\sigma^{54}$ promoter targets, indicating that the tool correctly identified $\sigma^{54}$ promoters in all cases. In addition, gel shift assays have shown that *M. xanthus* EBPs bind to 94% (33/35) of the $\sigma^{54}$ promoters identified using Promscan and are believed to work in conjunction with $\sigma^{54}$ to transcribe from $\sigma^{54}$.

BRIEF DESCRIPTION OF THE DRAWINGS

The present invention will be more fully understood and appreciated by reading the following Detailed Description in conjunction with the accompanying drawings, in which:

FIGS. 4A and 4B are LC-MS traces of E. coli fermentation extract after addition of 2 mM EDTA and adjustment to pH 2.0, of the oxytetracycline standard and E. coli extract, respectively.

DETAILED DESCRIPTION OF THE INVENTION

Figure 1A:
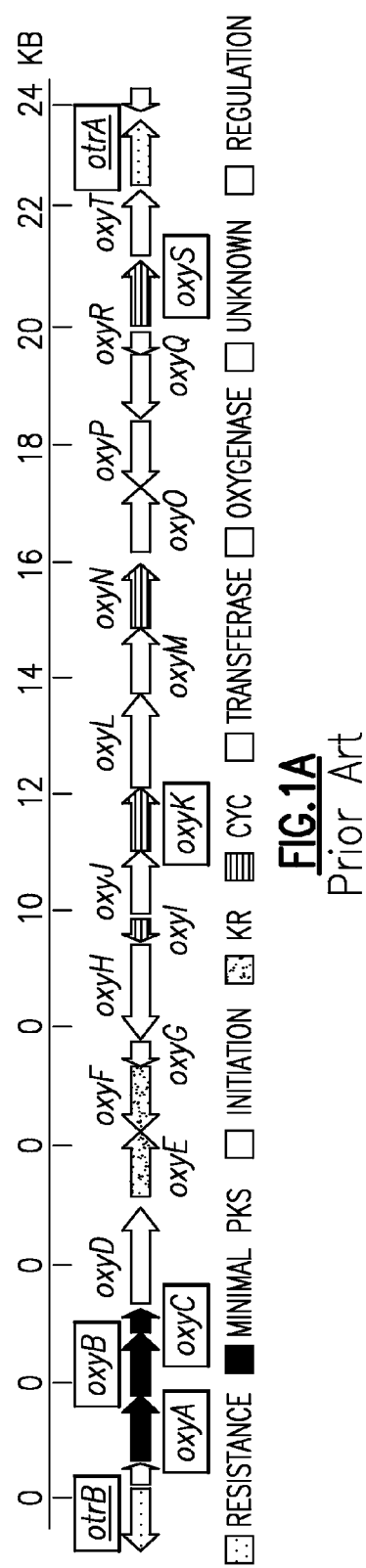
FIG. 1A is schematic of a gene cluster of oxytetracycline biosynthesis.
Figure 1B:
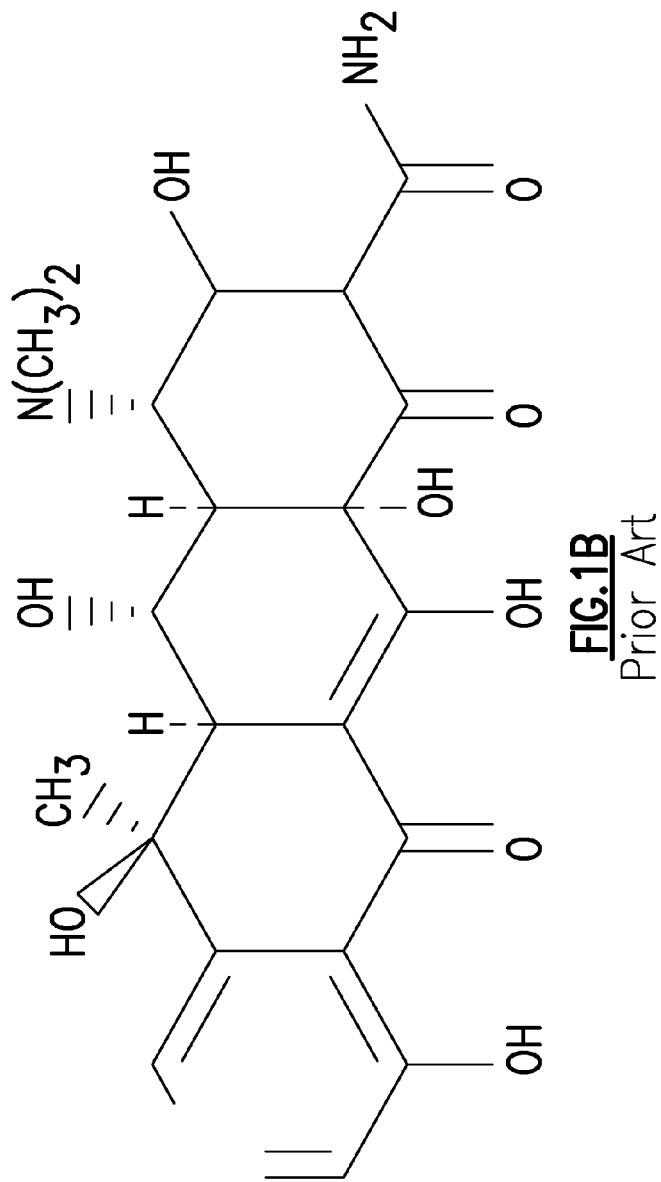
FIG. 1B is a chemical diagram of oxytetracycline.

Referring now to the drawings, wherein like numerals refer to like parts throughout, the present invention comprises the use of a highly conserved promoter system for the expression of polyketide and non-ribosomal peptide biosynthetic pathways. In particular, the present invention comprises the use of the $\sigma^{54}$ transcription system to increase the production of secondary metabolites by an organism by increasing the activity of σ54 dependent transcription. Increasing the activity of σ54 dependent transcription may be accomplished by genetically modifying a target organism to include a polymerase and a promoter upstream of an rpoN gene. For example, the expression of rpoN may be increased by placing a target gene under the control of the T7 promoter and providing a T7 RNA polymerase. Similarly, the activity of σ54 dependent transcription may be increased by increasing coactivation of a σ54-RNAP transcriptional complex bound to a σ54 promoter. Alternatively, the activity of σ54 dependent transcription may be increased by genetically modifying an organism to include a polymerase and a promoter upstream of a gene encoding an Enhancer Bind Protein (EBP), such as pspF. It should be obvious to those of skill in the art that an appropriately modified organism may then be cultured and processed according to known methods to isolate secondary metabolites produced by the organism.

As explained below, the system and method of the present invention was implemented in the host organism M. xanthus. M. xanthus is a predatory δ-proteobacterium that is able to lyse pro- and eukaryotes and grow on the released nutrients. During predation, M. xanthus releases polyketide antibiotics to kill bacterial prey. To deal with antibiotic resistant prey there was likely a strong evolutionary pressure for M. xanthus to obtain, via horizontal gene transfer, new antibiotic biosynthetic pathways. In order for these pathways to provide an increase in fitness, the genes must be transcribed. M. xanthus likely possessed a "universal" transcriptional activator system for the heterologous expression of polyketide and non-ribosomal peptide biosynthetic pathways. To test this theory, the present invention was used for the heterologous expression of a distantly related streptomyces-derived biosynthetic pathway in M. xanthus.

In particular, the present invention was adapted for the oxytetracycline biosynthetic pathway from Streptomyces rimosus. The oxytetracycline pathway is an archetypical example of an aromatic polyketide synthase biosynthetic pathway. The backbone of oxytetracycline is assembled from a minimal PKS consisting of four proteins a ketosynthase (KS), a chain length factor (CLF), an acyl transferase (AT), and an acyl carrier protein (ACP). The minimal PKS catalyses repetitive Claisen-like condensations using ten sequential units of malonyl-CoA. Following backbone production, a minimum of six tailoring enzymes completes oxytetracycline biosynthesis. Overall the biosynthesis requires over a dozen enzymes working in concert.

Example 1

Figure 2B:
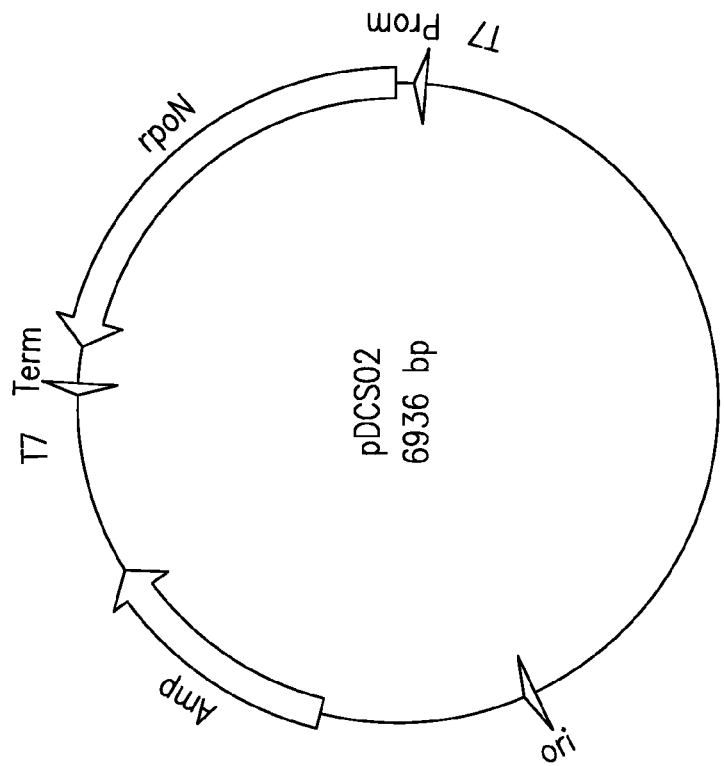
FIG. 2B is a schematic of pDCS02 with the rpoN gene from M. xanthus.
Figure 2A:
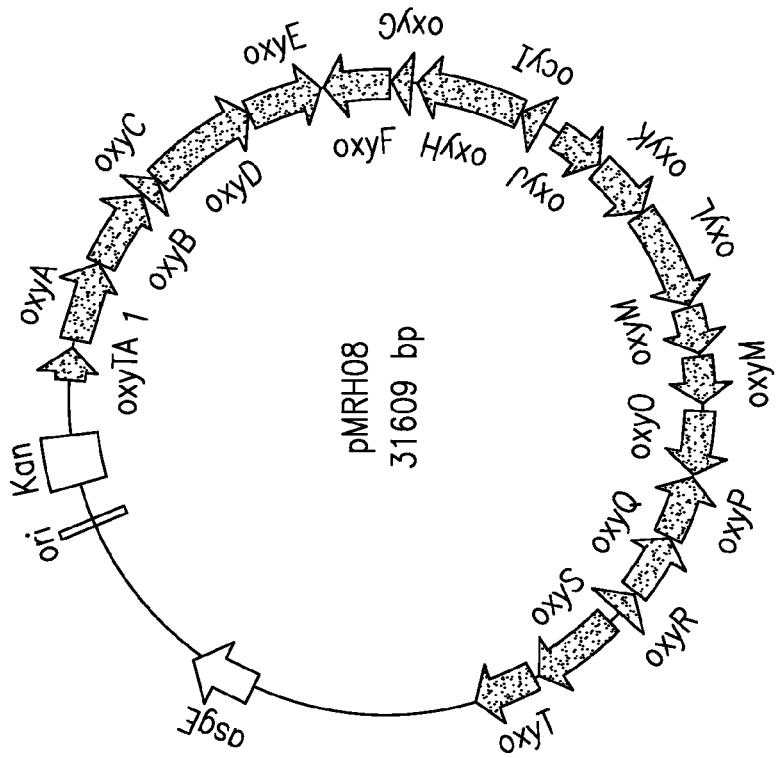
FIG. 2A is a schematic of pMRH08 with the oxytetracycline gene cluster from S. rimosus.

There is seen in FIG. 2A a pMRH08 with the oxytertracycline gene cluster from S. rimosus and, in FIG. 2B, pDCS02 with the rpoN gene from M. xanthus. Production of oxytetracycline from M. xanthus via homologous recombination demonstrates the ability of the non-native promoters from M. xanthus to recognize and initiate gene transcription of the oxytetracycline PKS from S. rimosus. The present may be used, among things, is connection with Myxococcus xanthus rpoN gene (SEQ ID No. 1), the Escherichia coli rpoN gene (SEQ ID No. 2), and the Pseudomonas putida rpoN gene (SEQ ID No. 3).

Figure 3A:
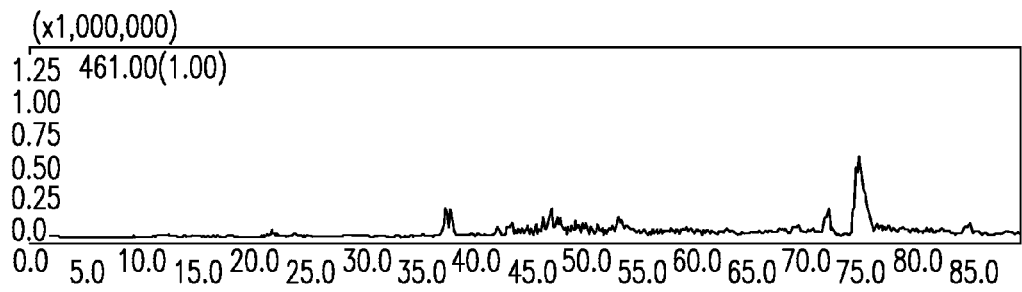
FIGS. 3A-3E are LC-MS traces of extracts of wild-type M. xanthus, M. xanthus plus pMRH08, the oxytetracycline standard, E. coli plus pMRH08, and E. coli plus pMRH08 and pDCS02, respectively.
Figure 3B:
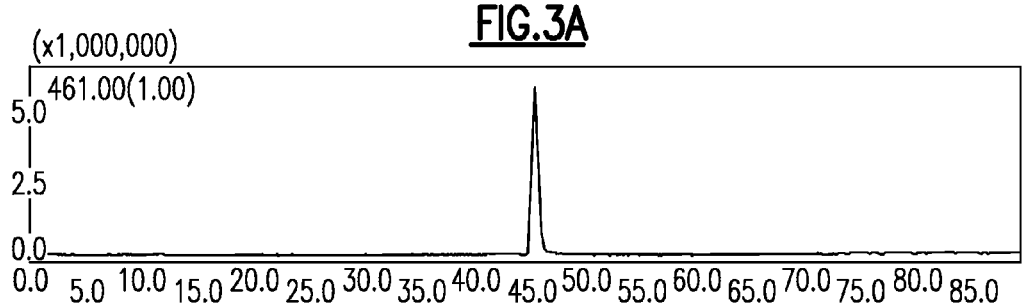
Figure 3C:
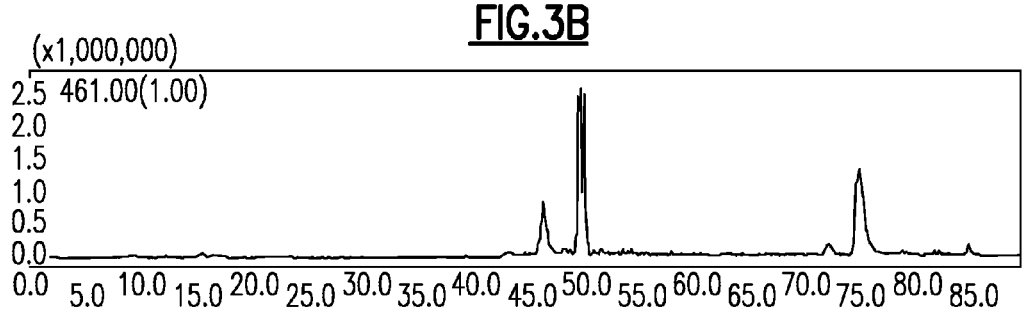

Production of oxytetracycline from M. xanthus strain DK1622 was observed using the pET28a expression vector, the 21 kb oxytetracycline biosynthetic pathway and the A-signal factor asgE from M. xanthus (pMRH08) (see FIG. 3A through 3C). The asgE region allows for homologous recombination of the oxytetracycline biosynthetic pathway into the chromosome of M. xanthus 22. Transformation of M. xanthus with pMRH08 was conducted using standard electroporation methods. Selection of specific mutants was provided via the kanamycin resistance marker located on the pET28a expression vector. Organic phase extractions using EtOAc were implemented to extract oxytetracycline for verification using LC-MS.

Example 2

If the M. xanthus $\sigma^{54}$ system is responsible for driving expression of the oxytetracycline gene cluster in M. xanthus, as discussed in Example 1, than expression of the M. xanthus $\sigma^{54}$ factor in E. coli should also drive expression of the oxytetracyline gene cluster. Accordingly, M. xanthus rpoN was cloned into a pET21 based expression plasmid, generating pDCS02. Plasmid DCS02 was developed using the pET21c expression vector with the rpoN gene amplified from M. xanthus inserted into the vector under an inducible T7 promoter. Plasmid DCS02 allows the expression of $\sigma^{54}$ promoters using heterologous expression. The relevant portion of the sequence of the σ54 promoter is TGGCACGNNNNTTGCW (SEQ ID No. 4), where N is any nucleotide and W represents A or T.

E. coli strain BL21 (DE3) was also transformed with the oxytetracycline gene cluster (pMRH08). This system severed as a negative control since the strain BL21(DE3) cannot post-translationally modify PKS proteins. E. coli strain BAP1 was obtained from Chaitan Khosla at Stanford University and transformed with pMRH08. This arrangement was designed to confirm that no background expression of the PKS pathway from the *S. rimosus* genomic DNA was occurring. Finally *E. coli* strain BAPI was co-transformed with pMRH08 and pDCS02. This arrangement was designed to test if *M. xanthus* $\sigma^{54}$ factor can function with the *E. coli* RNA polymerase to transcribe the polyketide synthase and tailoring genes responsible for oxytetracycline biosynthesis.

Figure 3D:
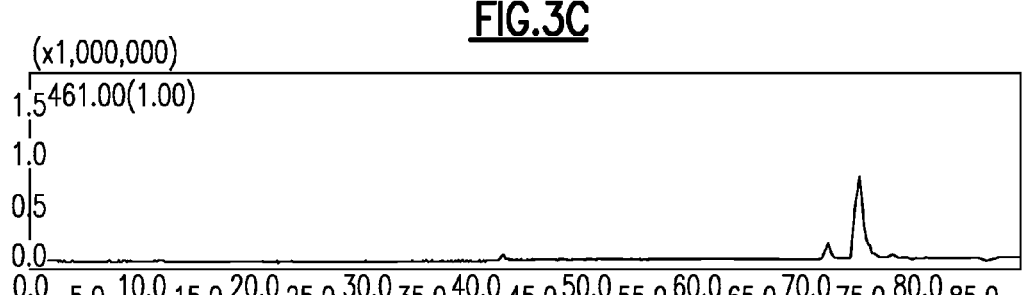
Figure 3E:
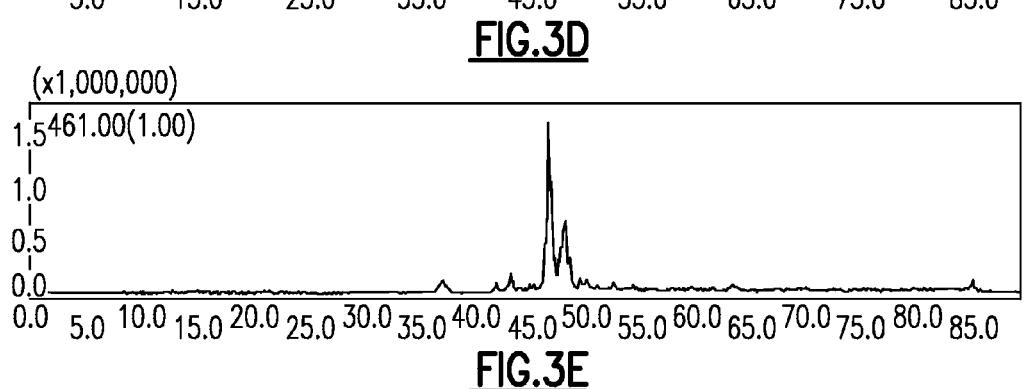
Figure 5A:
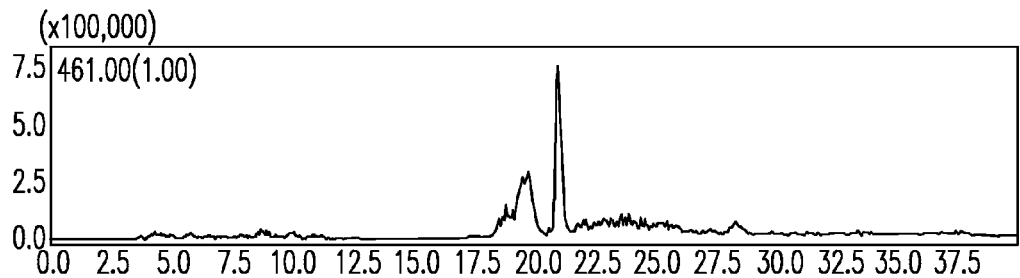
FIGS. 5A-5D are charts of LC-MS data from E. coli extract for titer calculations for: BAPI extract; BAPI extract +0.01 mg/ml oxytetracycline; BAPI extract plus 0.05 mg/ml oxytetracycline; BAPI extract plus 0.075 mg/mL oxytetracycline; respectively.
Figure 5B:
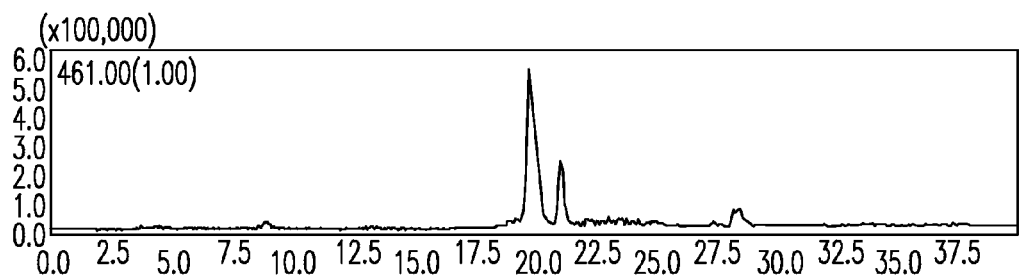
Figure 5C:
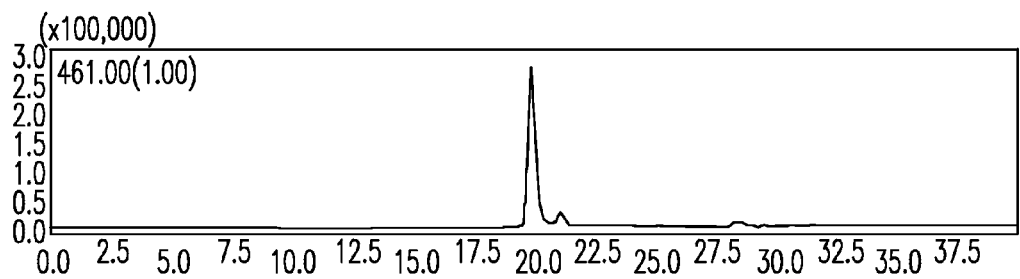
Figure 5D:
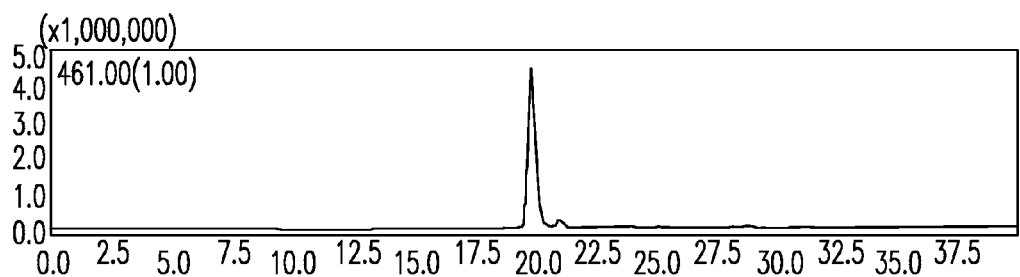
Figure 5E:
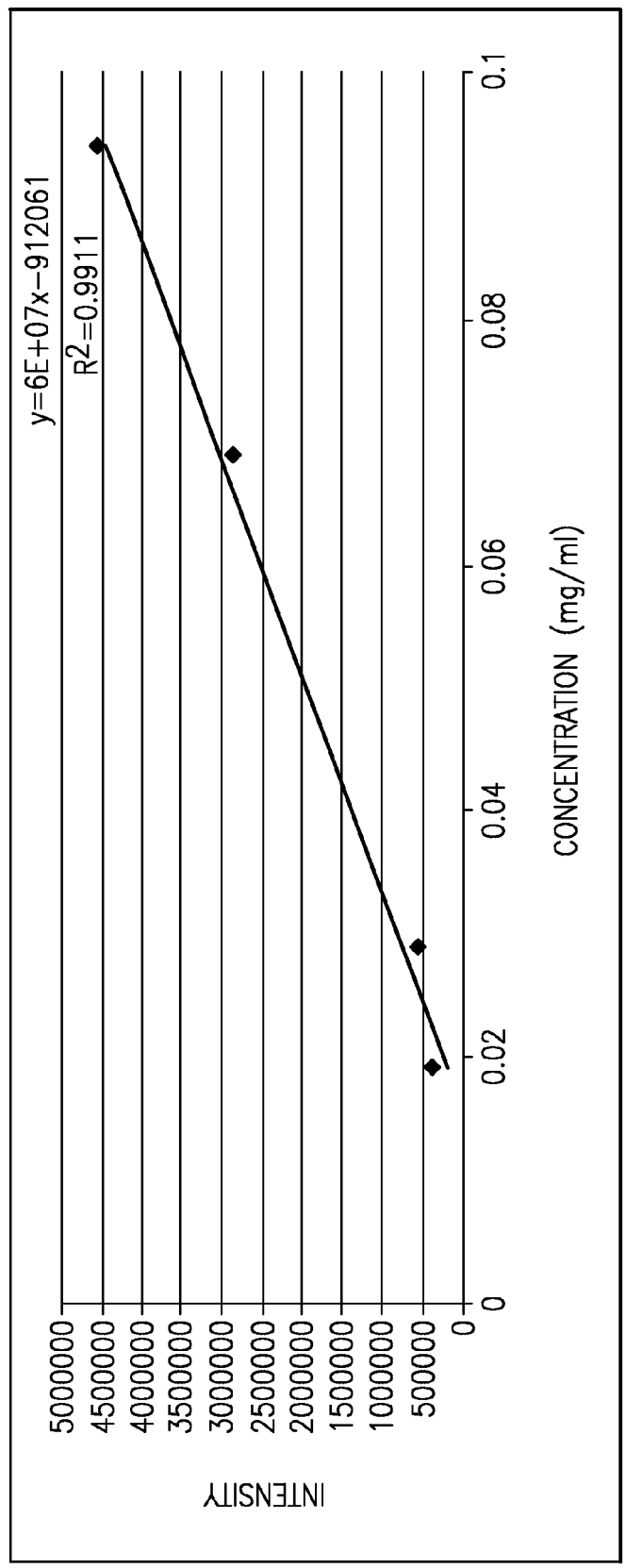
FIG. 5E is a plot of intensity versus concentration (mg/ml).

Transformations of *E. coli* strains BL21 and BAP1 were performed via electroporation with both pMRH08 and pDCS02 using kanamycin and ampicillin for selection. Both strains were inoculated with isopropyl β-D-1-thiogalactopyranoside (IPTG) at $OD_{60}=0.6$ to induce protein expression. Production of oxytetracycline was observed from simultaneous expression of rpoN from *M. xanthus* and the oxytetracycline gene cluster from *S. rimosus*, as seen in FIG. 3D. A potential isomer of oxytetracycline was also observed in the extracts from the BAP1 cultures. This isomer was not observed in fresh BAP1 fermentation broths at pH 2.0, as seen in FIG. 4. Although the preferred embodiment uses a lac operon induction system, other expression induction systems and factors can be utilized.

All strains were grown in rich media at 30° C. IPTG was added to a final concentration of 0.1 mM during log phase growth. Cells were harvested 60 h post induction, the media was extracted with Amberlyst XAD-16, and the organics were eluted from XAD-16 with methanol. LCMS analysis was used to assay for oxytetracycline production. The presence of oxytetracycline was confirmed by comparison with an authentic sample, identification of the $[M+H]^+$ and $[M+Na]^+$ peaks in the mass spectrum and co-injection with an authentic sample.

The extraction of oxytetracycline from aqueous media using organic solvents results in low yields (>40%). For means of isolation and purification, oxytetracycline was extracted using the non-polar absorber resin Amberlite XAD-16. This resin was added to the centrifuged fermentation broths and the aqueous broth was removed. The resin was eluted with MeOH and provided a three-fold increase in titers.

There is seen in FIGS. 4A and 4B, LC-MS traces of *E. coli* fermentation extract after addition of 2 mM EDTA and adjustment to pH 2.0, of the oxytetracycline standard and *E. coli* extract, respectively. Purification of oxytetracycline from fermentation broth also proved difficult. Extracts eluted from the Amberlite XAD-16 absorber resin were concentrated 100 fold for preparatory TLC. TLC plates were coated with a 10% EDTA solution at pH 9.0 to prevent oxytetracycline from chelating ionic metals, thus allowing movement of oxytetracycline on silica. A 60:35:5 solvent system comprised of dichloromethane, MeOH, and H20 was used. Oxytetracycline was extracted from silica using MeOH and greater purity was observed via LC trace.

Oxytetracycline titers were determined using known concentrations of oxytetracycline standard added into prepared extracts from both *M. xanthus* and *E. coli*. Comparisons of intensity change versus concentration provided by LC-MS after addition of standard into the extracts afforded titers of 6.4 mg/L and 1.5 mg/L produced in *M. xanthus* and *E. coli* respectively.

There is seen in FIGS. 5A through 5E, LC-MS data from *E. coli* extract for titer calculations for: BAPI extract; BAPI extract +0.01 mg/ml oxytetracycline; BAPI extract plus 0.05 mg/ml oxytetracycline; BAPI extract plus 0.075 mg/mL oxytetracycline; and a plot of intensity versus concentration (mg/ml); respectively.

*E. coli* was shown to have an inability to produce oxytetracycline after transformation with pMRH08, thereby confirming the *E. colis* promoter's inability to initiate gene transcription of the oxytetracycline PKS domain. On the other hand, the transformations of *E. coli* strains BL21 and BAP1 with pMRH08 were observed to produce oxytetracycline. It is believed that the *M. xanthus* $\sigma^{54}$ is designed to transcribe the GC rich sequences found in the oxytetracycline genes from *S. rimosus*. FIGS. 3A through E depicts LC-MS traces of extracts of wild-type *M. xanthus*, *M. xanthus* plus pMRH08, the oxytetracycline standard, *E. coli* plus pMRH08, and *E. coli* plus pMRH08 and pDCS02, respectively. Through production of oxytetracycline, the co-expression of pMRH08 and pDCS02 confirm *E. coli*'s ability to express and use the $\sigma^{54}$ protein from *M. xanthus* to express the oxytetracycline biosynthetic pathway from *S. rimosus*. This homologous recombination also provided the first production of a streptomycetes secondary metabolite from a myxobacterium. *E. coli* was not able to recognize the streptomycetes promoter regions using its native transcriptional machinery, and did not produce oxytetracycline after transformation with the oxytetracycline biosynthetic pathway. Co-expression of the transcriptional machinery from *M. xanthus* with the oxytetracycline biosynthetic pathway from *S. rimosus* enabled *E. coli* to recognize and express the oxytetracycline biosynthetic pathway and produce oxytetracycline. Thus, *E. coli* cells that over-express *M. xanthus* rpoN show a dramatic increase in the level of the product of the oxytetracycline biosynthetic pathway from *S. rimosus*.

These results indicate that promoter regions recognized by the σ54 transcription factor could be located upstream of all operons in the *S. rimosus* oxytetracycline gene cluster or only on essential synthetic genes. Alternatively, the $\sigma^{54}$ transcriptional factor may control expression of regulatory genes/proteins required for the expression of oxytetracycline.

Figure 6:
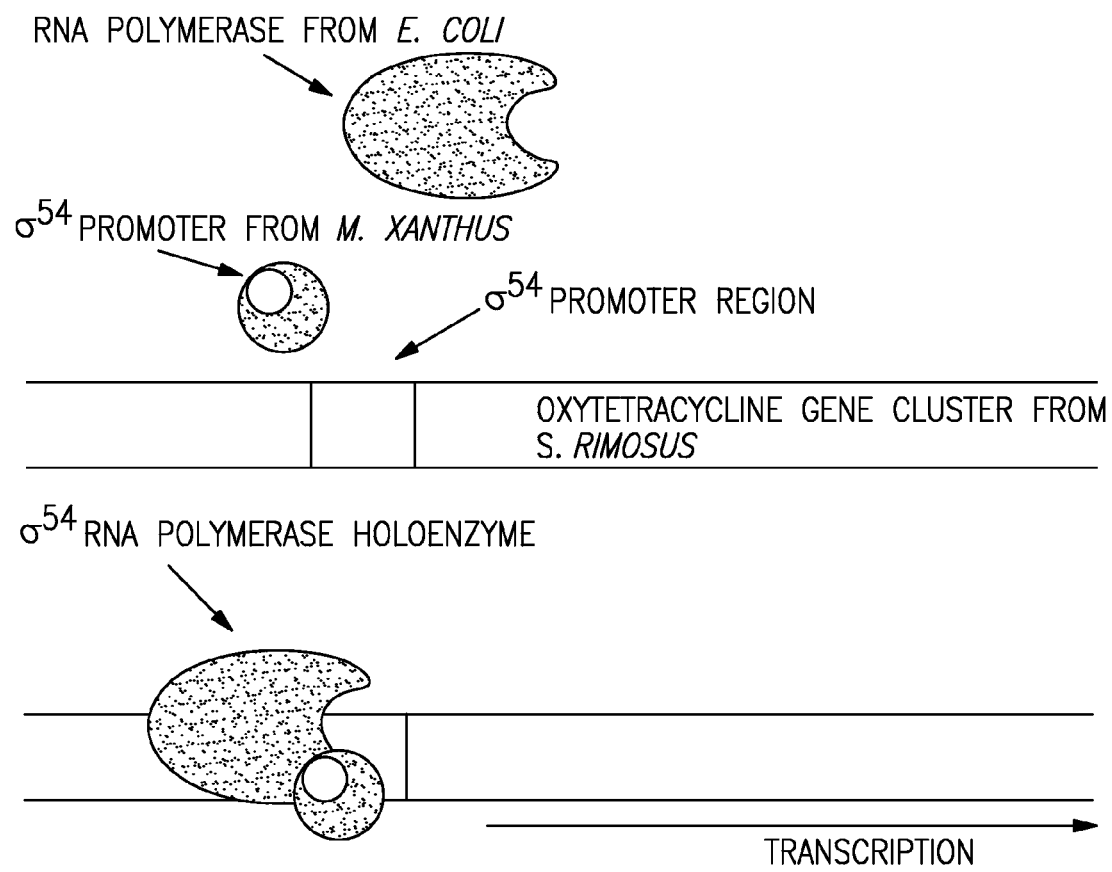
FIG. 6, is a schematic $\sigma^{54}$ directed transcription of the oxytetracycline gene cluster.

Referring to FIG. 6, transcription of a secondary metabolite gene cluster, such as the oxytetracycline gene cluster, may be accomplished by using the $\sigma^{54}$ transcription system in a host organism, such as *E. coli*. Using polyketide biosynthetic pathways co-expressed with the necessary transcriptional machinery, several of the obstacles associated with heterologous expression of polyketide biosynthetic pathways may be overcome. Production of polyketides from *E. coli* using heterologous expression thus provides a new and efficient approach to the production and discovery of polyketides.

Example 3

For the purposes of testing the present invention, *Myxococcus xanthus* strain DKI622 was used, and *E. coli* XLI-Blue was used for cloning purposes. *E. coli* BL21(DE3) was used as a negative control for expression of secondary metabolites due to its inability to post translationally modify PKS ACP domains. The present invention also used an *E. coli* strain BAPI containing the sfp gene from *Bacillus subtillis* allowing post-translational modification of PKS ACP domains and to generate functional PKS was used for oxytetracycline expression studies.

Cloning of pMRH08 was performed using pTY264 containing the oxytetracycline gene cluster provided by Yi Tang of the Department of Chemical and Biomolecular Engineering, University of California, Los Angeles. Plasmids were purified using the Wizard Plus SV Miniprep Kit, available from Promega. The asgE fragment was amplified from *M. xanthus* strain DKI622 using the following primers:

```
                                              (SEQ ID No. 5)
(forward)
5'-GACGAGATCTGTTGGAAGGTCGGCAACTGG-3'  (Bgl II)

(SEQ ID No.6)
(reverse)
3'-CTTAAGATCTTCCGTGAAGTACTGGCGCAC-5'  (Bgl II)
```

Restriction sites are shown in italics and the restriction enzymes are in parenthesis. The amplified asgE fragment was cloned into PCR Blunt according to the manufacturer's instructions (Invitrogen), generating plasmid pCNB02. The asgE fragment was sequenced for verification. pMRH06 was produced by subsequently cloning the asgE gene into the Bgl II site of pET28a (Novagen). pTY264 was digested with EcoR I to remove the included oxytetracycline gene cluster. The EcoR I oxytetracycline fragment was gel purified and ligated into pMRH06 which was previously digested with EcoR I and subsequently treated with calf-intestinal alkaline phosphatase.

Cloning of pDCS02 was accomplished by amplifying the rpoN gene from *M. xanthus* strain DK1622 using the following primers:

```
                                       (SEQ ID No. 7)
(forward)
5'-TGCGCATATGGCGATGGAACTGAAACAAAGC-3' (Nde I)
and (SEQ ID No. 8)
(reverse)
3'-TGCGGAATTCTCAGTAGTACCGCTTGCGCTT-5' (EcoR I).
```

The introduced restriction sites are shown in italics and the restriction enzymes are in parenthesis. The amplified rpoN gene was cloned into PCR Blunt according to the manufacturer's instructions (Invitrogen). The rpoN gene was sequenced for verification. pDCS02 was produced by subsequently cloning the rpoN gene into the Nde I and EcoR I sites of pET21c (Novagen).

*M. xanthus* was grown at 32° C. in CTTYE broth (1% Casitone, 0.5% yeast extract, 10.0 mM Tris-HCl (pH 8.0), 1.0 mM KHrP04, and 8.0 mM MgS04). Electroporated *M. xanthus* cells were recovered on 1.5% CTTYE plates supplemented with CTT soft agar (0.7% agar) for single colony isolation. CTTYE broths were supplemented with 40 µg kanamycin for selection when needed. *E. coli* cultures were grown in Luria-Miller broth, which was supplemented with kanamycin and ampicillin as needed. Fermentation of *E. coli* was conducted in F1 media (3 g $KH_2PO_4$, 6.62 g $K_2HPO_4$, 4 g $(NH_4)_2SO_4$, and 150.5 mg $MgSO_4$ in per liter amounts).

The fermentation and extraction techniques for *M. xanthus* involved the use of a pre-culture of *M. xanthus* that was grown for 5-7 days from which 500 µL was used to inoculate a 100 mL culture. After 7-10 days cells were collected and 10 mL of acetone was added and applied to a vortex mixer for 45 seconds. Three equal volumes of EtOAc were added, and the aqueous layer was discarded. The organic layer was washed with saturated NaCl, and the aqueous layer was removed. The organic layer was dried with anhydrous sodium sulfate, filtered, and evaporated to dryness. The residue was dissolved in MeOH with 1/10 the original culture volume.

Fermentation of *E. coli* was started in 150 mL of pre-made Luria-Miller broth supplemented with kanamycin and ampicillin and induced with IPTG (0.1 mM) at $OD_{600}$=0.6 and incubated for 6 hours. Cells were then harvested and re-suspended in F1 media supplemented with kanamycin, ampicillin and IPTG (0.1 mM) allowed to incubate at 37 degrees C. for 60 hours. Cells were centrifuged and removed. After centrifugation, 2 mM EDTA was added to the fermentation broth. The pH of the fermentation broth was adjusted to 1.8 with 3M HCl. After pH adjustment, Amberlite XAD-16 (2% m/v) was added to the fermentation broth and gently stirred for two hours. Fermentation broth was then filtered and removed from the resin. Resin was washed with excess water and eluted with 5 mL MeOH.

For initial confirmation of oxytetracycline cells at $OD_{600}$=0.6 were collected and 10 mL of acetone was added and applied to a vortex mixer for 45 seconds. Three volumes of EtOAc were then added and the aqueous layer was discarded. The organic layer was washed with saturated NaCl and the aqueous layer was removed. The organic layer was then dried with anhydrous sodium sulfate and concentrated to 10× by rotary evaporation.

TLC plates were previously coated with a 10% EDTA solution at pH 9.0 to prevent oxytetracycline from chelating ionic metals, allowing movement on silica. A 60:35:5 solvent system comprised of dichloromethane, MeOH, and $H_2O$, respectively, was used for separating oxytetracycline. Oxytetracycline was extracted from silica using MeOH.

Figure 7:
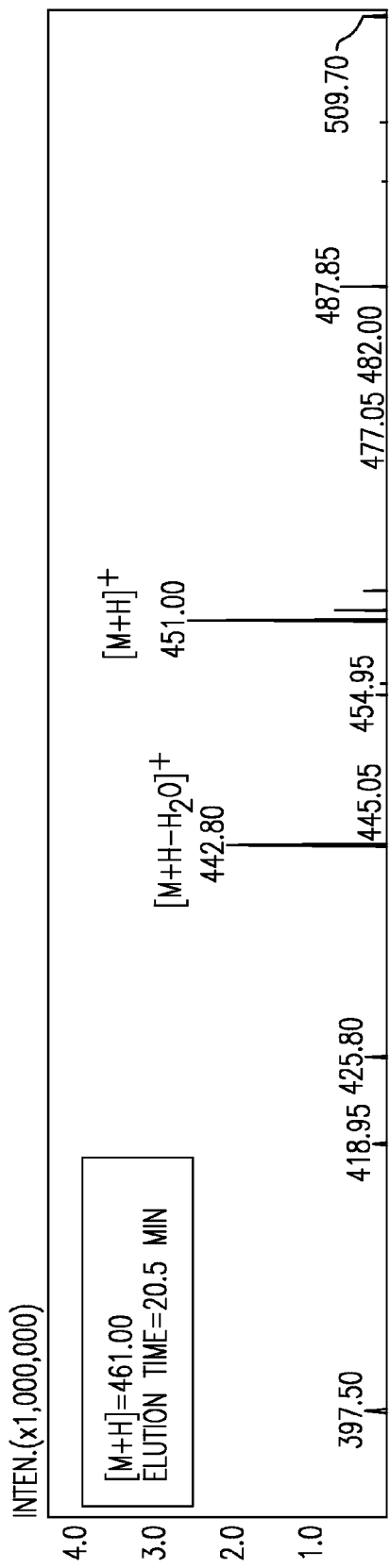
FIG. 7 is a graph of a mass spectrum of the oxytetracycline standard.

LC-MS was performed on a Shimadzu LCMS 2010 A single quadrupole mass spectrometer using positive electro spray ionization according to the following: Alltima LC-MS C18 column, 3 u, 150 mm×2.1 mm; Mobile phase A, 5.0% acetonitrile, 0.05% formic acid in H20; Mobile phase B, 5.0% H20 0.05% formic acid in acetonitrile: Flow rate, 0.100 mL min-1; gradient 1: 10 min at 0% B then a linear gradient from 0% B to 95% B over 90 min, gradient 2: 8 min at 0% B then a linear gradient from 0% B to 95% B over 40 min. Oxytetracycline standard eluted at 45.2 min with gradient 1 and 20.5 min with gradient 2. MS (ESI) calculated for oxytetracycline [M+H]=461.00. In FIG. 7, a mass spectrum of the oxtetracycline standard is shown.

Enhancer binding proteins ("EBP") are DNA-binding proteins that allow $\sigma^{54}$-loaded RNA polymerase to form a transcriptionally-active open promoter complex. Each EBP has a specific DNA recognition sequence that helps it identify target $\sigma^{54}$ promoters. Since the *E. coli* in the previous examples were able to produce polyketides without heterologous EBPs, the native *E. coli* EBP was able to recognize a promoter of *S. rimosus* oxytetracycline genes to promote $\sigma^{54}$ RNA polymerase-dependent transcription at these promoters. There are 12 *E. coli* EBPs, any one or more of which could interact with the promoters of *S. rimosus* oxytetracycline genes. In one embodiment of the present invention, one or more of *E. coli*'s 12 EBPs are over-expressed to increase the production of the polyketide synthases. In another embodiment, the rpoN gene contains one or more mutations that render the $\sigma^{54}$ protein EBP-independent. This approach renders expression of polyketide synthases in *E. coli* cells independent of native EBPs. For example, specific mutations in the rpoN gene have been shown to render the $\sigma^{54}$ protein EBP-independent.

The proposal that secondary metabolites from a variety of bacterial species can be produced by $\sigma^{54}$-mediated hereologous expression is supported by bioinformatics data; In the 90 bacterial species that were examined, $\sigma^{54}$ promoters were computationally identified upstream of over 90 percent of the secondary metabolite biosynthetic operons, as described below. The promoters identified by the present invention are functional $\sigma^{54}$ promoters and directly regulate transcription of secondary metabolite biosynthetic genes, which confirms that computationally identified $\sigma^{54}$ promoters can be used to produce secondary metabolites by heterolgous expression.

Figure 8:
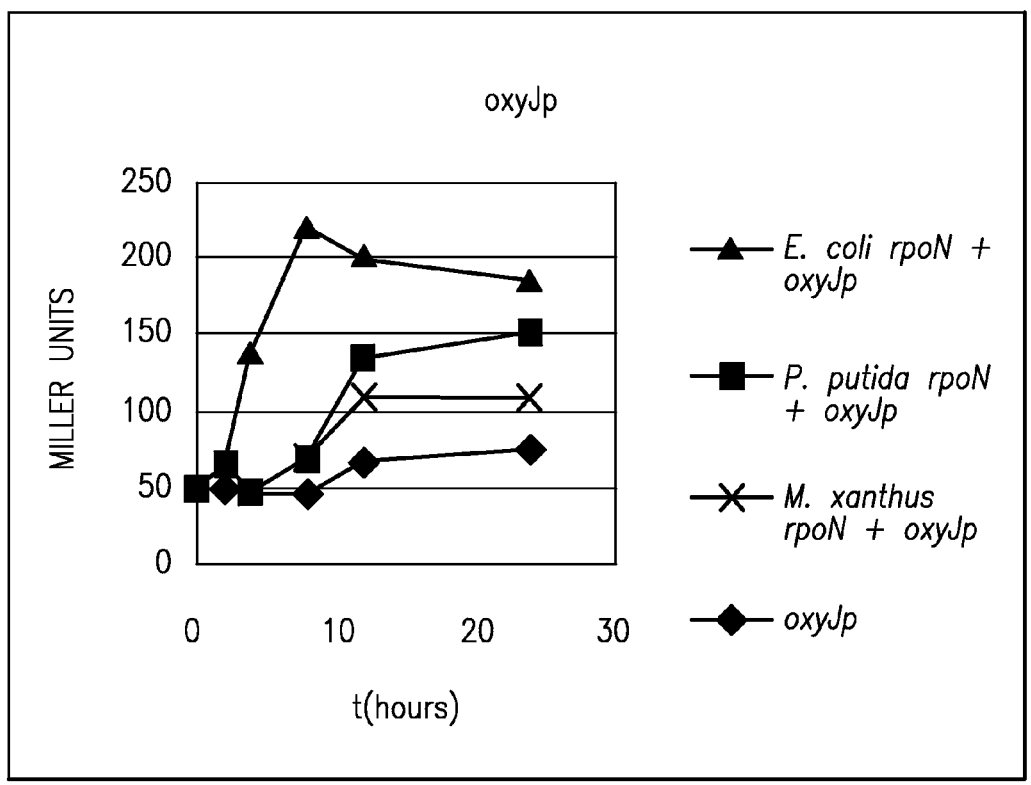
FIG. 8 is a graph of β-galactosidase activity determined at multiple time points.

Potential $\sigma^{54}$-RNAP DNA binding regions were located in each target biosynthetic pathways using Promscan (http://molbiol-tools.ca/promscan/). The Promscan predicted oxyJp from the oxytetracycline biosynthetic pathway was submitted to a promoter activity assay for authentication. The oxyJ promoter (oxyJp) possessed a stringent Promscan confidence score (>75) and a Promscan predicted enhancer binding protein (EBP) site within 500 bp from the promoter. The oxyJp was placed upstream of the β-galactosidase gene to generate a transcriptional reporter system (SEQ ID No. 9). The transcriptional reporter system was transformed into *Escherichia coli* JM109(DE3) containing rpoN orthologs (from either *E.* coli, Myxococcus xanthus, Pseudomonas putida) under the control of an inducible T7 promoter. Expression of rpoN was induced and β-galactosidase activity was determined at multiple time points (see FIG. 8). Production of $\sigma^{54}$ (the gene product of rpoN) led to a significant increase in β-galactosidase activity versus the negative controls (no rpoN over-expression), indicating increased transcription form the $\sigma^{54}$ promoter. This data indicates that oxyJp is a $\sigma^{54}$-RNAP dependent promoter and are consistent with $\sigma^{54}$ promoters mediating direct regulation of secondary metabolite biosynthesis. This data also indicates that the computationally predicted $\sigma^{54}$ promoters are functional and can be used to directly regulate transcription of secondary metabolite biosynthetic pathways. Thus, this data confirms that a promoter is present in the proposed location upstream of oxyJp and, as a result, $\sigma^{54}$ over-expression is important for transcription of oxyJp.

Gel shift assays performed thus far have shown that *M. xanthus* EBPs bind to 94% (33/35) of the σ54 promoters identified using Promscan. Use of the Promscan bioinformatics tool reveals that all of the 17 operons in the *M. xanthus* genome sequence have putative $\sigma^{54}$ promoters located upstream of the first gene in the operon. An additional search for putative $\sigma^{54}$ promoters that drive transcription of polyketide and non-ribosomal peptide biosynthetic operons was similarly successful. Using the Promscan bioinformatics tool, eight additional bacterial species known to be major producers of natural products were assessed for putative $\sigma^{54}$ promoters. Representatives from the myxobacteria, *Streptomyces, Pseudomonas, Mycobacterium* and *Bacillus* species were analyzed. Including those found in *M. xanthus*, a total of 117 operons that are annotated as polyketide biosynthesis components or non-ribosomal peptide biosynthesis components were analyzed and found to include putative $\sigma^{54}$-like promoters upstream of the first gene in all of these operons (see Table 1 below showing putative $\sigma^{54}$ promoters upstream of the natural product biosynthetic genes in major producing bacterial species where only those operons annotated as polyketide biosynthesis components or non-ribosomal peptide biosynthesis components were examined using Prom Scan).

TABLE 1

| Organism | Number of natural product biosynthetic operons examined* | Percent having $\sigma^{54}$-like promoters |
| --- | --- | --- |
| *Sorangium cellulosum* | 21 | 100% |
| *Myxococcus xanthus* | 17 | 100% |
| *Streptomyces avermitilis* | 16 | 100% |
| *Streptomyces coelicolor* | 14 | 100% |
| *Pseudomonas fluorescens* Pf-5 | 14 | 100% |
| *Pseudomonas putida* KT 2440 | 13 | 100% |
| *Pseudomonas syringae* DC 3000 | 9 | 100% |
| *Mycobacterium tuberculosis* CDC 1551 | 8 | 100% |
| *Bacillus subtilis* | 5 | 100% |

This data suggests that, in bacteria, $\sigma^{54}$ promoter-driven transcription of polyketide and non-ribosomal peptide biosynthetic operons may be conserved.

To further examiner this conservation of $\sigma^{54}$ promoter-driven transcription of polyketide and non-ribosomal peptides, operons with the annotation polyketide biosynthesis or non-ribosomal peptide biosynthesis were examined in bacterial species from fourteen different groups (see Table 2 below showing a summary of putative $\sigma^{54}$ promoters found upstream of natural product biosynthetic genes in different groups of bacteria and in archaea, where only those operons annotated as polyketide biosynthesis components or non-ribosomal peptide biosynthesis components were examined using PromScan). The genomes of bacteria from five of these groups did not contain operons with the appropriate annotations. Seventy five bacterial genomes from the nine remaining groups were scanned and a total of 219 operons with polyketide biosynthesis or non-ribosomal peptide biosynthesis annotations were found.

TABLE 2

| Bacterial group/Archaea | Number of species analyzed | Number of natural product biosynthetic operons examined** | Percent having $\square^{54}$-like promoters |
| --- | --- | --- | --- |
| Archaea | 28 | 3 | 33 |
| Acidobacteria | 1 | 6 | 100 |
| Actinobacteria* | 11 | 80 | 100 |
| Aquificae | 1 | 0 | — |
| Bacteroidetes/Chlorobi | 6 | 2 | 100 |
| Chlamydiae/Verrucomicrobia | 5 | 0 | — |
| Chloroflexi | 4 | 0 | — |
| Cyanobacteria | 5 | 6 | 100 |
| Deinococcus-Thermus | 4 | 1 | 100 |
| Firmicutes* | 18 | 20 | 100 |
| Fusobacteria | 1 | 0 | — |
| Planctomycetes | 1 | 3 | 100 |
| Proteobacteria* | 22 | 96 | 100 |
| Spirochaetes | 7 | 2 | 100 |
| Thermotogae | 2 | 0 | — |

Based on PromScan analysis, 100 percent of these natural product biosynthetic operons have potential $\sigma^{54}$ promoters. While false positives may occur, in previous studies in *M. xanthus* we used similar PromScan bioinformatics tool parameters and all eighteen of the putative $\sigma^{54}$ promoters that Promscan identified were confirmed. Thus, the results are highly indicative of $\sigma^{54}$ promoter control of bacterial polyketide biosynthetic operons and non-ribosomal peptide biosynthetic operons is highly conserved.

Since eukaryotes do not use the $\sigma^{54}$ system, the promoter analysis was not extended to eukaryotic organisms. A scan of the genome sequences of 28 species of archaea found only three operons with polyketide biosynthesis or non-ribosomal peptide biosynthesis annotations. These findings suggest that these two classes of natural product biosynthetic operons are not very common among the archaea whose genomes have been sequenced and perhaps among the archaea in general. Of the three operons that have the appropriate annotations, only one putative $\sigma^{54}$ promoter was identified using PromScan. With such a limited number of examples, it is difficult to draw any conclusions about $\sigma^{54}$ system control of polyketide and non-ribosomal peptide biosynthetic operons in archaea.

Prophetic Example 1

The scope of $\sigma^{54}$-mediated transcriptional activation of polyketide and non-ribosomal peptide biosynthetic pathways can be further evaluated by determining if $\sigma^{54}$ can boost transcription of the type I polyketide synthase pathway for the biosynthesis of aureothin, the type II polyketide synthase pathway for the biosynthesis of actinorohdin, and the NRPS pathway for the biosynthesis of nocardicin A. This evaluation can involve the ability of *E. coli* and *B. subtilis* $\sigma^{54}$, in addition to *M. xanthus* $\sigma^{54}$, to boost transcription of these biosynthetic pathways in both *E. coli* and *M. xanthus*.

Determining the scope of $\sigma^{54}$-mediated heterologous expression of natural product biosynthetic pathways is a key step in developing a "universal" heterologous expression system. By examining the major types of bacterial biosynthetic pathways, type I PKS, type II PKS and NRPS containing pathways, the scope of the natural products accessed by the present invention can be determined. Screening $\sigma^{54}$ factors from two of the major families of natural product producing bacteria (myxobacteria and *bacillus*) as well as *E. coli* will enable determination if different a factors may be better suited to different types of biosynthetic pathways. Lastly screening both *E. coli* and *M. xanthus* as hosts offers flexibility to implementation of the present invention. While *E. coli* is advantageous because of its favorable growth characteristics, *M. xanthus* may provide superior titers of the natural product, as was seen for heterologous expression of oxytetracycline.

Prophetic Example 2

Another useful test of the heterologous expression of different natural product biosynthetic pathways in *E. coli* overexpressing *M. xanthus* $\sigma^{54}$ is to determine whether *E. coli* over-expressing *M. xanthus* $\sigma^{54}$ can produce via heterologous expression a variety of different types of natural products. The key reagents required for this experiment are plasmids containing the entire biosynthetic pathways for the three compounds discussed above.

Aureothin is a type I or modular polyketide produced by *Streptomyces thioluteus*. The compound shows anti-tumor, anti-fungal and insecticidal properties. The biosynthetic pathway is 27 kb and encodes nine ORFs, one of which is a transcription factor. The cosmid containing the aureothin biosynthetic gene cluster (pST18E4) may be requested from Christian Hertweck. Alternatively the 27 kb coding region can be PCR amplified from the gDNA of the aureothin producing strain *Streptomyces mobaraensis*, which is available from the ATCC (ATCC 25365), and cloned into a blunt end cloning vector with a kanamycin selectable marker.

Actinorhodin is a type II or aromatic polyketide produced by *Streptomyces coelicolor*. A BAC (StBAC28G1) may be obtained from the John Innes center containing the complete 16 kb actinorhodin biosynethtic pathway. Because of the large size of the BAC (approximately 250 kb) PCR amplifying of the entire pathway and cloning it into the blunt end cloning vector with a kanamycin selectable marker may be performed.

Nocardicin A is a non-ribosomal peptide β-lactam compound produced by *Nocardia uniformis*. Its biosynthetic gene cluster is 33 kb in size and code for fourteen proteins, including a single transcriptional activator. The nocardicin A biosynthetic pathway may be PCR amplified from the genome of *N. uniformis*, which is available from the ATCC (ATCC 21806). The 33 kb fragment may be ligated into a blunt end cloning vector with a kanamycin selectable marker to generate the required plasmid.

Plasmids containing the biosynthetic pathways for these compounds may be transformed into BAP1/pDCS02. Strains may be grown under conditions described in the earlier example and $\sigma^{54}$ expression will be induced by the addition of 0.1 mM IPTG. Cells may be harvested 60 h post induction and the organic components extracted using XAD-16. The crude organic extracts may be eluted from the XAD-16 with methanol and then subjected to LCMS analysis. Chromatography conditions as described by He and Hertweck (2003) may be used to separate aureothin and the LC conditions described by Gunsior et al. (2004) will be used to separate nocardicin A. Standard LC conditions will be used to separate actinorohdin. Compounds will be initially characterized by mass spectrometry and unambiguously confirmed via isolation followed by $^1$H and $^{13}$C NMR spectroscopy. If over-expression of $\sigma^{54}$ is a conserved mechanism for heterologous expression of natural product biosynthetic pathways, these compounds will be successfully produced in *E. coli*.

Prophetic Example 3

The present invention may be further understood by testing different $\sigma^{54}$ factors for their ability to mediate heterologous expression oxytetracycline biosynthetic pathways in *E. coli* to determine if *M. xanthus* $\sigma^{54}$ is unique or if $\sigma^{54}$ from other organisms can mediate heterologous expression of the oxytetracycline pathway. This experiment will determine whether *M. xanthus* $\sigma^{54}$ is not unique and that over-expression of any $\sigma^{54}$ should mediate heterologous expression of the oxytetracycline pathway. To test this, overexpression of the *E. coli* and *B. subtilis* $\sigma^{54}$ can be performed.

Crucial reagents for this experiment are the inducible expression vectors containing the *E. coli* rpoN and *B. subtilis* rpoN. Both may be amplified off of the corresponding organisms' genomic DNA and cloned into pET21 vector. Plasmids containing *E. coli* and *B. subtilis* rpoN may be co-transformed with pMRH08 into BAP1. Strains may be grown under conditions described in the preliminary results and $\sigma^{54}$ expression will be induced by the addition of 0.1 mM IPTG. Cells will be harvested 60 h post induction and the organic components extracted using XAD-16. The crude organic extracts will be eluted from the XAD-16 with methanol and then subjected to LCMS analysis. Oxytetracycline may be detected and quantified as described in the preliminary results.

*E. coli* and *B. subtilis* $\sigma^{54}$ are expected to mediate heterologous expression of the oxytetracycline biosynthetic pathway with similar efficacy (titer) to the *M. xanthus* $\sigma^{54}$. It is possible that only the *M. xathus* $\sigma^{54}$ can mediate heterologous expression of the oxytetracycline pathway, but this would be an unexpected result as the GC content of $\sigma^{54}$ promoters is similar across bacterial species.

Prophetic Example 4

The present invention may be further tested with respect to the heterologous expression of different natural product biosynthetic pathways in *M. xanthus* to evaluate the titer of *E. coli*-based heterologous expression with *M. xanthus*-based heterologous expression. Preliminary results showed that *M. xanthus*-based heterologous expression produced 3-4 fold higher oxytetracycline titer that the *E. coli*-based system. Comparing the titer between the different hosts for the three compounds discussed above will enable determination whether one host is reliably better or if the optimal host is compound dependant.

Key reagents for this experiment are plasmids containing the biosynthetic pathways for the three compounds as well as a 1 kb fragment of the *M. xanthus* asgE locus. The asgE locus enables the plasmid to insert via homologous recombination into the genome of *M. xanthus*. The plasmids constructed for the heterologous expression of the compounds in *E. coli* may be cut with the EcoR I sites that flank the inserts. The gene cluster containing inserts may then be cloned into the EcoR I site of the asgE containing pET28 vector constructed in the preliminary results to provide the required plasmids.

*M. xanthus* DK1622 may be transformed with the three plamids containing the biosynthetic pathways of the three compounds. Cultures may be grown under standard conditions for ten days and the organic components of the media isolated via extraction. LCMS may be used to assay for the presence of the three compounds as previously described. The *M. xanthus*-based heterologous expression system is expected to produce the three compounds and comparison to the *E. coli*-based system will determine if one host is clearly superior.

Prophetic Example 5

The present invention may be tested to determine the effect of enhancer binding protein over-expression on the level of polyketide and non-ribosomal peptide production to optimize rpoN overexpression systems in *E. coli* and *M. xanthus* to boost transcription of natural product biosynthetic genes derived form other bacterial species and, presumably, to boost production of the corresponding natural products. In addition to RpoN, the $\sigma^{54}$ system requires an EBP to activate transcription at $\sigma^{54}$ promoters. Specifically, EBPs are required for $\sigma^{54}$-RNA polymerase to form an open promoter complex and to initiate transcription. Preliminary work on the *Streptomyces rimosus* oxytetracycline gene cluster suggest that an EBP from *E. coli* (no EBP gene was found in the oxytetracycline gene cluster) is capable of recognizing the promoter of *S. rimosus* oxytetracycline genes and promoting $\sigma^{54}$ RNA polymerase-dependent transcription at this promoter. EBPs typically bind to tandem repeat sequences located well upstream of the −24 and −12 regions of $\sigma^{54}$ promoters. Preliminary scanning of the putative $\sigma^{54}$ promoters in the *S. rimosus* oxytetracycline gene cluster revealed tandem repeat sequences, a finding that supports the proposal that an *E. coli* EBP is participating in transcription of the oxytetracycline genes from *S. rimosus*. These results are a testament to the conservation and flexibility of the $\sigma^{54}$ system. That is, over-expression of *M. xanthus* rpoN in *E. coli* cells, which harbor only native *E. coli* EBPs, seems to result it increased levels of transcription of the *S. rimosus*-derived oxytetracycline gene cluster.

Given that an *E. coli* EBP has been implicated in the rpoN over-expression-induced increase in the biosynthetic product of the *S. rimosus* oxytetracycline gene cluster, the first set of experiments proposed above will explore whether over-expressing the genes for EBPs might boost production of natural products in *E. coli* cells. Subsequent experiments may be used to determine whether over-expression of any of *E. coli*'s 12 EBP genes leads to an increase in transcription of the *S. rimosus* oxytetracycline genes and an increase in the levels of oxytetracycline. These experiments would reveal whether it might be feasible to boost heterologous natural product production by EBP over-expression alone. The *S. rimosus* oxytetracycline gene cluster may also be used to examine the effect that co-over-expressing EBP genes and rpoN might have on natural product production in *E. coli* cells. The rational for these studies is that over-expression of an EBP alone may not be sufficient to increase expression of natural product biosynthetic gene clusters that use $\sigma^{54}$ promoters, or that expression of $\sigma^{54}$ promoter-driven biosynthetic genes might be optimal when the appropriate EBP gene is co-expressed with rpoN. It should be noted that although similar heterologous *M. xanthus* EBP over-expression systems might yield relatively high levels of some natural products, over-expression studies in *M. xanthus* cells are straightforward but time consuming because *M. xanthus* has 53 EBPs. That is, a thorough pilot EBP over-expression study in *M. xanthus* would require construction of many more strains than for a similar *E. coli* study.

The examples described above will also explore whether one can construct a heterologous system that does not require EBPs for transcription at the $\sigma^{54}$ promoter elements of natural product biosynthetic genes. Certain mutations in *E. coli* rpoN render transcriptional activation by $\sigma^{54}$-RNA polymerase independent of an enhancer binding protein. In vitro and in vivo experiments indicate that RNA polymerase carrying these altered forms of $\sigma^{54}$ recognize $\sigma^{54}$ promoter elements and activate transcription at these promoters in an EBP-independent manner, although it was reported that the level of transcription at $\sigma^{54}$ promoters is reduced when compared to a wild-type $\sigma^{54}$ system. Construction of *E. coli* strains that over-express these EBP-independent rpoN alleles and examination whether they lead to an increase in transcription of the *S. rimosus* oxytetracycline genes and an increase in the levels of oxytetracycline would be informative. In addition, experiments using a *M. xanthus* strain that over-expresses a putative EBP-independent versions of *M. xanthus* rpoN may be used.

Prophetic Example 6

The present invention may be further evaluated by developing and testing *E. coli* systems that over-express EBP genes and that co-overexpress EBP genes and rpoN to determine whether over-expression of *E. coli* EBP genes alone or in conjunction with *E. coli* rpoN increases the transcriptional and product output of natural product biosynthetic gene clusters in heterologous *E. coli* systems. As mentioned above, preliminary studies indicate that an *E. coli* EBP is capable of functioning with $\sigma^{54}$-RNA polymerase to activate transcription of *S. rimosus* oxytetracycline genes that have been introduced into *E. coli* cells. Therefore, it is possible to test whether over-expression of any of *E. coli*'s 12 EBP genes boost *S. rimosus* oxytetracycline gene transcription and oxytetracycline production in *E. coli*. To do this, each EBP gene may be cloned into a vector with an inducible promoter and introduced into *E. coli* cells. Subsequently, a compatible plasmid carrying the *S. rimosus* oxytetracycline gene cluster under control of native *S. rimosus* promoters may be introduced into the 12 EBP gene-over-expressing strains. After expression of the EBP genes is induced, one may monitor the levels of EBP gene mRNAs using real-time QPCR and/or slot blot hybridization analysis as described previously, which will allow confirmation that EBP gene expression increases after induction. To test whether EBP gene induction increases the transcriptional output of the putative $\sigma^{54}$ promoters in the oxytetracycline gene cluster, monitoring expression of the *S. rimosus* oxytetracycline genes during EBP gene induction using the same techniques may be performed. In addition, one may monitor the levels of oxytetracycline in the induced *E. coli* strains as described above, which will tell us whether we get a boost in oxytetracycline production after we over-express the EBP genes. Subsequently, one may use the above strategy to examine the transcriptional and biosynthetic outputs of additional natural product gene clusters including aureothin, actinorohdin, and nocardicin A. These experiments will help determine whether the EBP gene over-expressing *E. coli* strains might be of general use for production of polyketides and non-ribosomal derived peptides.

To examine how co-overexpression of *E. coli* EBP genes and *E. coli* rpoN affects transcription of natural product biosynthetic genes and production of their biosynthetic products in *E. coli* cells, one may generate plasmids that allow dual induction of *E. coli* EBP genes and the *E. coli* rpoN gene. Generation of these plasmids using dual gene expression systems such as the Novagen Duet Vector system. Subsequent experiments will be conducted as described above and the results will be compared to those generated by over-expressing the EBP genes alone. Hence, one can determine which over-expression strategy generated optimal natural product production.

Prophetic Example 7

The present invention may further be evaluated by developing and testing *E. coli* and *M. xanthus* systems that over-express EBP-independent rpoN alleles. The rpoN (the gene encoding the $\sigma^{54}$ protein) mutations may be created using commercially available site-directed mutation kits such as GeneTailor (Invitrogen) or GeneEditor (Promega). The rpoN mutant alleles may be cloned into a vector with an inducible promoter and introduced into an K colt rpoN strain (By using the rpoN mutant, we will eliminate the possibility of promoter and RNA polymerase binding competition between wild-type $\sigma^{54}$ and the altered $\sigma^{54}$ proteins). For these experiments, a compatible plasmid containing *S. rimosus* oxytetracycline genes and their native promoters may be introduced into the *E. coli* strains that carry only the rpoN mutant alleles. After expression of the rpoN mutant alleles is induced, one may monitor the levels of the mutant rpoN mRNAs using real-time QPCR and/or slot blot hybridization analysis as mentioned above. To examine whether induction of the mutant *E. coli* rpoN genes increases the transcription of oxytetracycline genes, one may follow expression of the *S. rimosus* oxytetracycline genes after induction of the mutant rpoN alleles. The levels of oxytetracycline in the induced *E. coli* strains may be determined as described in the preliminary results. A similar strategy may be used to examine the transcriptional and biosynthetic outputs the biosynethtic gene clusters for the three compounds discussed above. Since it is possible that the altered $\sigma^{54}$ proteins have different preferences for $\sigma^{54}$-like promoters than wild-type $\sigma^{54}$ protein, these experiments will help determine the general applicability of our heterologous *E. coli* systems.

*M. xanthus* $\sigma^{54}$ contains the amino acids that correspond to L26 and L33 in the *E. coli* $\sigma^{54}$ protein. Therefore, one may generate an *M. xanthus* $\sigma^{54}$ protein that carries the L26S, L33S double amino substitution. However, the *M. xanthus* $\sigma^{54}$ protein lacks leucine residues at positions 31 and 37, which will prevent making a triple amino substitution. The appropriate double mutation in *M. xanthus* rpoN may be created by using commercially available site-directed mutation kits as mentioned above. This mutant rpoN allele may be introduced into a vector carrying the light-inducible carQRS promoter system. When growing cultures of *M. xanthus* cells are kept in the dark, the carQRS promoter is almost completely inactive. In contrast, exposing cells to blue light causes the carQRS promoter to become highly active. Hence, under conditions of vegetative growth carQRS is an ideal inducible promoter system. Since there are no plasmids available that replicate autonomously in *M. xanthus*, a plasmid carrying the carQRS promoter-controlled rpoN mutant allele and attP, which allows the plasmid to integrate into the Mx8 phage attachment site (attB) in the *M. xanthus* chromosome, may be introduced into wild-type *M. xanthus* cells via electroporation. Cells with the appropriate antibiotic resistance may be screened for plasmid integration at the Mx8 attB site in the chromosome using Southern blot analysis or PCR. As mentioned above, a vector containing the *S. rimosus* oxytetracycline gene cluster and a fragment of the *M. xanthus* asgE locus may be created, which allows the plasmid to be integrated into the *M. xanthus* chromosome by homologous recombination. This plasmid may be introduced into the *M. xanthus* strain carrying the inducible rpoN mutant allele via electroporation and cells with the appropriate antibiotic resistance properties may be analyzed using Southern blot analysis or PCR to confirm the location and structure of the plasmid integration events. Once the desired strain is generated, it will be tested for expression of the rpoN mutant allele, for expression of *S. rimosus* oxytetracycline genes and for production of oxytetracycline as described above for the heterologous *E. coli* systems. Subsequent experiments may involve: cloning additional known natural product gene clusters into the asgE locus-containing vector, introducing the plasmids into the *M. xanthus* strain that over-expresses the mutant rpoN gene, and testing the newly created strains for natural product gene transcription and natural product production as described above.

It should be noted that rpoN is an essential *M. xanthus* gene and, therefore, the experiments mentioned here are not possible in a *M. xanthus* rpoN mutant for technical reasons. In addition, electroporations done with high-concentration plasmid preparations often yield multiple plasmid insertions in the target locus in the *M. xanthus* chromosome. Accordingly, it is feasible to increase the copy numbers of plasmid-borne genes by doing electroporations with high-concentration plasmid preparations; electroporants can be screened for multiple plasmid insertions in the target locus. Using this strategy, it might be possible to increase expression of the rpoN mutant allele and/or the natural product biosynthetic gene cluster under consideration.

Prophetic Example 7

The present invention may be used to develop a method to screen BAC-based gDNA libraries for polyketide and non-ribosomal peptide production and determine the breadth of natural products that can be produced via $\sigma^{54}$-mediated heterologous expression and to optimize the expression system to maximize the titer of the target natural product. As an example, an *E. coli* based system for production of polyketide and non-ribosomal peptides directly from gDNA may be designed. Because of the large size of many PKS and NRPS gene clusters (>100 kb), a bacterial artificial chromosome (BAC) based system may be used to introduce gDNA fragments of 250 kb into *E. coli*. Over-expression of $\sigma^{54}$ will drive transcription of the gene cluster, leading to metabolite production.

As the *E. coli* strain used for heterologous expression above, BAP1, is not compatible with the use of BACs, an *E. coli* strain for a BAC-based heterologous expression system must be developed. The large inserts fond in BAC can be unstable to RecA, thus BACs are generally propagated and maintained in recA⁻ strains. BAP1 is not a recA⁻ strain and thus present an obstacle for the use of BACs. A recA⁻ strain for BAC-based heterologous expression of polyketide and non-ribosomal peptide biosynethtic pathways must have a number of key features. It should be based on a B strain, which are naturally ompT⁻ and lon⁻. The decreased protease activity of ompT⁻ and lon⁻ strain should maximizes expressed protein lifetime, increasing titer. It must have a T7 polymerase inserted into the genome to support protein expression under control of the T7 promoter. To ensure that PKS and NRPS proteins get posttranslationally modified, it must have a copy of sfp under the T7 promoter. The preferred location for sfp is incorporated into the genome. It should also have *M. xanthus* rpoN under the control of the T7 promoter inserted into the genome to enable heterologous expression of PKS and NRPS biosynthetic pathway. Placing rpoN and sfp in the chromosome as opposed to having them extrachromosomal simplifies transformation of the strain with the BAC.

Lastly, the strain should be recA⁻. To generate this strain one may start with BL21(DE3), which are lon⁻, ompT⁻, and have a copy of the T7 polymerase. Using lambda red mediated gene replacement, a bicistronic operon under the control of the T7 promoter containing *M. xanthus* rpoN and *B. subtilis* sfp in addition to the tetracycline resistance selectable marker may be inserted into recA.

The *E. coli* strain for heterologous expression of a polyketide biosynethtic pathway from a BAC may then be tested. The strain constructed above may be transformed with a BAC containing the actinorhodin pathway (StBAC28G1), available from the John Innes Center. *E. coli* may be grown and induced as described previously. Actinorohdin will be extracted from the media and quantified by LCMS as described in specific aim 1. Detection of actinorhodin indicates that the *E. coli* strain can support BACs, heterologously express PKS pathways and correctly post-translationally modify the PKS proteins.

A *S. natalensis* BAC library may then be constructed and screened for clones that produce pimaricin to demonstrate that $\sigma^{54}$-mediated heterologous expression can be used to produce natural products from BAC based gDNA libraries. *Streptomyces* natalensis was selected as the genome to screen because it contain a sequenced biosynthetic gene cluster but the organisms itself has not been sequenced. The *S. natalensis* biosynthetic gene cluster for pimaricin biosynthesis was sequenced in 2000 and spans 85 kb with 16 open reading frames. The large size of this cluster necessitates the use of BACs and the large number of potential operons provides a rigorous test for the $\sigma^{54}$-mediate heterologous expression system.

The key reagent required for this experiment is a BAC library of *S. natalensis* gDNA. For successful heterologous expression of the pimaricin gene cluster, a BAC must possess the entire biosynthetic pathway. To maximize the likelihood of a BAC containing the complete pathway, large inserts of 250 kb may be used. The construction of the BAC library will follow standard protocol. *S. natalensis* gDNA may be partially digested with BamH I and fractionated by pulsed-field gel electrophoresis. 200-250 kb DNA fragments will be recovered by electroelution, ligated into linearized pCC1BAC vector (Copy Control BAC Cloning kit), and electroporated into the *E. coli* host developed above. 2000 clones will be archived in 96 well microtiter plates. This represents 50× coverage of the genome based on a 8 Mb genome and 200 kb average insert size.

Library screening will occur in two stages. A first round PCR based screen will be used to identify clones containing the pimaricin thioesterase domain. Positive clones will then be assayed by LCMS for production of pimaricin. This will demonstrate that the conserved $\sigma^{54}$ promoter system can be harnessed to identify large complex biosynthetic gene clusters from gDNA libraries.

Prophetic Example 8

The present invention may also be implemented through a pilot-scale test of a metagenomic DNA library screen for new antitumor polyketide and non-ribosomal peptides to demonstrate at pilot-scale that metagenomic DNA libraries can be heterologously expressed and screened for bioactive compounds. Because of the incredible complexity and diversity present in a metagenomic DNA sample, automation is required to adequately sample the library. A sampling will provide key information on the percent of clones possessing NRPS or PKS genes, the percent of clones producing antitumor metabolites, and an estimate of the frequency of duplicate bioactive metabolites. This data will be critical in evaluating the feasibility of scaling this approach to natural product discovery to the high-throughput level.

Soil possesses enormous untapped bacterial diversity, with upwards of 10,000 bacterial species present in a soil sample. Because less than 1 percent can be cultured a culture independent method of accessing this diversity is required. Metagenomic DNA libraries can capture this diversity in a culture independent manner. One may thus construct a metagenomic DNA library from soil for screening according to the present invention.

Soil may be collected in the Sven Heiberg Memorial Forest and Tully Field Station, State University of New York, Environmental Science and Forestry and metagenomic DNA isolated following standard literature protocols. The BAC library will be constructed as described above. 2000 clones will be archived in 96-well microtiter plates. This library represents approximately 400 Mb of metagenomic DNA.

Library screening will occur in two stages. 500 clones will be analyzed with degenerate PCR to identify if PKS or NRPS sequences are present. To detect the presence of PKS genes, the following ketosynthase specific primers will be used:

```
                                        (SEQ. ID. No. 10)
5'-MGNGARGCNNWNSMNATGGAYCCNCARCANMG-3'
and (SEQ. ID. No. 11)
5'-GGRTCNCCNARNSWNGTNCCNGTNCCRTG-3').
```

To identify NRPS genes, adenylation domain specific primers may be used as follows:

```
                                        (SEQ. ID. No. 12)
5'-GGWCDACHGGHAANCCHAARGG-3'
and (SEQ. ID. No. 13)
5'-GGCAKCCATYTYGCCARGTCNCCKGT-3'.
```

PKS and NRPS positive clones will be further screened for antitumor activity. The positive clones may be cultured at 10 mL scale. Cultures $\sigma^{54}$ over-expression will be induced with 0.1 mM IPTG and cultures harvested 60 h post induction. XAD-16 resin (100 mg) will be added to the culture broth and incubated 2 h at 30° C. The culture broth will be removed and the organics eluted from the XAD-16 with 2004 methanol, providing the crude organic extracts. Based on heterologous expression levels of approximately 1 mg/L of culture and an average metabolite molecular weight of 500 g/mol, the crude stock should have approximately 1 mM metabolite. This working stock should be sufficiently concentrated to use for antitumor assays.

Antitumor activity may be determined via a cell-based MTT antitumor assay. Compound displaying activity may be analyzed by LCMS. To facilitate identification of the bioactive components, two LCMS data sets will be compared, the crude bioactive extract and a negative control generated from over-expressing $\sigma^{54}$ in the presence of a BAC with no insert. The negative control strain should have similar *E. coli* derived components as the crude bioactive extract. It should though differ in the components heterologously expressed from the BAC. To compare the data sets, peak tables containing retention time and m/z of the parent ion may be generated for the negative control and crude bioactive extracts. Peaks unique to the crude bioactive metabolite will be assigned as potential metabolites.

The present invention thus provides new approaches to natural product chemistry and provides for tapid isolation of and characterization of natural product gene clusters from unculturable organisms. The present invention also provides a method for production of useful quantities of natural products from unculturable organisms, including symbionts, and provides increased access to chemical diversity (10-100 fold increase) by producing natural products from a substantial more diverse set of bacteria. This present invention also provides a promoter system that has the potential to provide a general solution to convenient, fast, high-yielding heterologous expression of natural product biosynthetic pathways. Although the present invention has been described in connection with various embodiments, it should be understood that modifications, alterations, and additions can be made to the invention without departing from the scope of the invention as defined by the claims.

What is claimed is:

1. A genetically modified host organism for expressing a target polyketide, comprising:
   a first modification comprising the addition of a non-native gene cluster that encodes for the target polyketide biosynthetic pathway;
   a second modification comprising the addition of an rpoN gene from *Myxococcus xanthus*; and
   a third modification comprising the addition of an inducible promoter positioned upstream of and operatively associated with the rpoN gene added to said host organism.

2. The organism of claim 1, further comprising a gene encoding an RNA polymerase.

3. The organism of claim 1, wherein the organism is at least one organism selected from the group consisting of *Escherichia coli, Streptomyces rimosus, Streptomyces lividans, Streptomyces coelicolor Myxococcus xanthus, Pseudomonas putida*, and *Bacillus subtilis*.

4. The organism of claim 1, wherein the rpoN gene comprises SEQ. ID. No. 1.

5. The organism of claim 1, wherein the promoter comprises a T7 promoter.

6. The organism of claim 1, wherein the target polyketide comprises oxytetracycline.

* * * * *

SEQUENCE LISTING

<160> NUMBER OF SEQ ID NOS: 13

<210> SEQ ID NO 1
<211> LENGTH: 1517
<212> TYPE: DNA
<213> ORGANISM: Myxococcus xanthus

<400> SEQUENCE: 1

```
atggcgatgg aactgaaaca aagcctgaag cttgcccaac agctggtgat gacgccgcag      60
ctgcagcaag ccatcaagct cctccaactg tctcgcatgg aactgctcga gcaggtccgc     120
gaggagatgg agcagaaccc gctgctggag caaccagacg agcaagcgcc gggggatgtg     180
ggagacaagg aacccgggga agcctccctg gaagcagaca acatggaggt gccgcgggac     240
gtggatctgc ccgcggccac cagcgacacc gccacggagt tcaaggcgga cggggagggc     300
cccccggaaa tcgactggga gcagtacctc aacagctacc agttcaatga gcccaccacg     360
gcctccaaca agggcaacgt ggccacggac gacatgccgt cgttcgaggc caacctcgtc     420
aagaaggcgg acctggtcga ccacatccag gagcagctgg gcacgctgcg cctgaatgac     480
gccgagcgcc gcatcgccat gctcatcctg ggcaacctgg atgacgacgg ctacctcaag     540
ctgccggaag tggacgggga tccgctcatc cgcctggcca acgaggcgga cgtgcccatg     600
cacgtcgcgg agcgcacgct gcggcgcatc cagatgttgg atccgcgcgg ctgcggcgcc     660
cgtgacttgc aggagtgcct gctcatccag ctccagggca tcagggagcc gcacgcgccg     720
ctgttgggcc tcatcatcaa gcggcacatg aagtacctgg agagcaagaa cctgcccgcc     780
atcgccaagg acctgaaggt caccttggaa gaggtggtgg gggcggtgcg gctgctcccg     840
aagctggacc cgaagccggg ccgcaacttc agcggggacg acgcgcagta catctccccc     900
gacgtgttcg tctacaagat gggggacgac tacacggtgg tgctcaacga tgacggcctg     960
tccaagctgc gcatctccgg cacctaccgg aacgcgctga gacgggcgc ggtgggcccg    1020 ggccagacga aggacttcat ccaggacaag ctgcgcagcg cgatgtggct catccgctcc    1080
atccaccagc ggcagcggac catctacaaa gtcaccgaag catcgtgaag ttccagcggg    1140
acttcctgga caagggcatt gcctacctca agccgctcat cctccgggac gtggccgagg    1200
acatcggcat gcacgagtcc acggtgagcc gcgtcaccac cagcaagtac gtgcacacac    1260
cgcagggcat cttcgagctg aagtacttct tcaactcgtc catcgcccgc gtctccggtg    1320
aggacaccgc gagcgaggcg gtgaagcacc acatcaagca gttggtggcg caggaagacg    1380
cccgcaaccc gtactcggac cagaaaatcg tcgagctgct gcgctcgcag ggcaccgaga    1440
ttgcccgccg cacggtggcc aagtaccgcg aggtgctggg catcctcccc agcagcaagc    1500
gcaagcggta ctactga                                                  1517
```

<210> SEQ ID NO 2
<211> LENGTH: 1434
<212> TYPE: DNA

<213> ORGANISM: Escherichia coli

<400> SEQUENCE: 2

```
atgaagcaag gtttgcaact caggcttagc caacaactgg cgatgacgcc acagctccaa      60
caggcaattc gtctgttgca gttgtcgacg ctggaacttc agcaggagct acagcaggcg     120
ctggagagta atccgctgct tgagcaaatc gacactcatg aagaaatcga cacccgcgaa     180
acgcaagaca gtgaaacgct ggacaccgcc gacgcgctcg aacaaaaaga gatgccggaa     240
gagctgccgc tcgatgccag ttgggacacc atttacaccg ctggtacacc atccggcacc     300
agcggtgact acattgacga cgagctgccg gtctaccagg cgaaacgac gcagaccttg      360
caggattacc tgatgtggca ggttgagctg acaccgtttt ccgacactga ccgcgctatt     420
gctacctcta tcgtcgatgc cgttgatgaa accggttatc tgactgtccc gctggaagat     480
attctcgaaa gtataggcga tgaagagatc gacatcgacg aagttgaagc cgtccttaag     540
cggatccaac ggtttgatcc ggtcggtgtg gcggcaaaag atctgcgtga ctgtctgctg     600
atccaactct cccaattcga taagaccacg ccgtggctgg aagaggccag actgatcatt     660
agcgatcatc tcgatctgtt agccaatcac gacttccgca ctttaatgcg cgtcacgcgt     720
ctgaaagaag atgtgctgaa agaagccgtc aatctgatcc agtcgctcga tccgcgcccc     780
gggcagtcga tccagactgg cgaacctgag tatgtcattc cagatgtgct ggtgcgtaag     840
cataacggtc actggacggt agaactcaac agtgacagca ttccgcgtct gcaaatcaac     900
cagcactacg cctcgatgtg caataacgcg cgcaacgatg tgacagcca  gtttatccgc     960
agcaatctgc aggatgccaa atggttgatc aagagtctgg aaagccgtaa cgatacgcta    1020
ctgcgcgtga gtcgctgtat cgttgaacag cagcaagcct tctttgagca aggtgaagaa    1080
tatatgaaac cgatggtact ggccgatatc gcccaggctg tcgaaatgca tgaatcgacg    1140
atatctcgcg tgaccacgca aaaatacctg catagtccac gaggcatttt tgaactgaag    1200
tatttctttt ccagtcacgt caataccgag ggcggcggcg aagcttcctc cacggcgatt    1260
cgtgcgctgg tgaagaaatt aatcgcggcg gaaaacccag cgaaaccgtt gagcgacagc    1320
aagttaacct ctttgctgtc ggaacaaggt atcatggtgg cacgccgcac tgttgcgaag    1380
taccgagagt ctttatccat tccgccgtca aaccagcgta acaactcgtt tga           1434
```

<210> SEQ ID NO 3
<211> LENGTH: 1494
<212> TYPE: DNA
<213> ORGANISM: Pseudomonas putida

<400> SEQUENCE: 3

```
ctacatcagt cgcttgcgtt cgctcgacgg tgcgatgccg agggactcgc ggtacttggc      60
gacggtgcga cgggctacct ggatgccttg tgcctccagt aaaccagcga tcttgctgtc     120
actcaatggc ttttctctgat tttccgccgc aaccagtttc ttgatgatcg cgcggatcgc     180
cgtggacgag cattctccgc cttcggaggt gctgacatgg ctggagaaaa agtatttcag     240
ttcgtagatg ccacgcgggg tgtgcatgta tttctgcgtg gtaacccgcg aaatggtcga     300
ttcgtgcatg cctacggctt cggcaatgtc atgcagtacc aacggcttca tcgcttcgtc     360
gccgtggtcg aggaagccgc gctggtgctc gacgatctgc gtggcaacct tcatcagggt     420
ttcgttacgg ctttgcaggc tcttgatgaa ccagcgcgct tcctgcagct ggttgcgcat     480
gaaggtgttg tcggcgctgg tgtcggcacg gcgcacgaag ccggcgtatt gtgggttgac     540
gcgcaggcgt gggatggctt cctggttcag ttctaccagc caacggtcgc tgtccttgcg     600
```

```
cacgatgacg tcgggcacca cgtactcggg ctcgctggac tcgatctgcg aaccagggcg    660
cgggttaagg ctttgcacca gttcgatgac ctggcgcagc tcgtcttcct tgattttcat    720
ccgccgcatc agctggctgt agtcacggct gccgagcagg tcgatgaaat cggtgaccag    780
gcgcttggct tcggtcatcc acggagttgt agcgggcagc tggcgcagtt gcagcaacag    840
gcattcgccg aggttgcggg cgccaacgcc agccggctcg aactgctgga tgcggtgcag    900
taccgcttcg acctcgtcca gttcgatatc cagctccggg tcgaaaccgg cgcagatttc    960
ttcgagtgtg tcttccaggt agccctggcc gttgatgctg tcgatcaggg tcacggcaat   1020
caagcggtcg gtgtcggaca tcggtgccag gttcaactgc acagcaggt ggctttgcag   1080 gctttcgccg gccgatgtgc gcgtggtgaa gtcccattcg tcgtcatcgt tgctcggcag   1140
gctgctggcg ctggtctggt agatgtcttc ccaagcggta tcgaccggga gctcgttggg   1200
gatgcgctcg ctccactcac cgtcttccag gttgtcggcg ctgacggtgc tttcctggaa   1260
actgttgtcc tgaacttcgg cggccggctt gttctcggcg ttgtcggcca tcgggtcgct   1320
gttgtcgaag tcttcgccgt cttcctgacg ttcgagcatc gggttcgact ccagcgcttc   1380
ctggatttcc tgttggaggt ccagggtaga aagctggagc aggcggatgg cctgttgcaa   1440
ctgaggtgtc atcgtcagtt gctggcccat ttttaggacg agcgatggtt tcat          1494
```

<210> SEQ ID NO 4
<211> LENGTH: 16
<212> TYPE: DNA
<213> ORGANISM: Myxococcus xanthus
<220> FEATURE:
<221> NAME/KEY: misc_feature
<222> LOCATION: (8)..(11)
<223> OTHER INFORMATION: n is a, c, g, or t

<400> SEQUENCE: 4
tggcacgnnn nttgcw                                                     16

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
gacgagatct gttggaaggt cggcaactgg                                      30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
cttaagatct tccgtgaagt actggcgcac                                      30

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
tgcgcatatg gcgatggaac tgaaacaaag c                                    31

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
tgcggaattc tcagtagtac cgcttgcgct t                            31

<210> SEQ ID NO 9
<211> LENGTH: 3444
<212> TYPE: DNA
<213> ORGANISM: Artificial Sequence
<220> FEATURE:
<223> OTHER INFORMATION: Promoter

<400> SEQUENCE: 9

| | | | | | | |
|---|---|---|---|---|---|---|
| gcatgccctt | gtcctccggt | gttgtggtct | gcggtgggcg | cgctcgcgcg | gcgcccgtcc | 60 |
| ggccgggcgg | acccaggcgc | tgcctcgccc | gtcccgtacg | ccccagcctg | caagggcccg | 120 |
| ttcgaggctg | gaccgaccgc | ggttggggcg | gtctccgtgc | ggcgcggcgg | ggcgatcacg | 180 |
| gaccgaccac | ggctcgaaga | acggtcgaag | accggctgcc | acgctcacgc | cgagcggccg | 240 |
| cccccagccc | ggccgctcta | gaaataattt | tgtttaactt | taagaaggag | atataccatg | 300 |
| ggcagcgcta | gccatcatca | tcatcatcac | agcagcggcc | tggtgccgcg | cggcagccat | 360 |
| atggctaatg | accatgatta | cggattcact | ggcgtcgttt | tacaacgtcg | tgactgggaa | 420 |
| aaccctggcg | ttacccaact | taatcgcctt | gcagcacatc | cccctttcgc | cactggcgta | 480 |
| atagcgaaga | ggcccgcacc | gatcgccctt | cccaacagtt | gcgcagcctg | aatggcgaat | 540 |
| ggcgctttgc | ctggtttccg | gcaccagaag | cggtgccgga | agctggctg | gagtgcgatc | 600 |
| ttcctgaggc | cgatactgtc | gtcgtcccct | caaactggca | gatgcacggt | tacgatgcgc | 660 |
| ccatctacac | caacgtgacc | tatcccatta | cggtcaatcc | gccgtttgtt | cccacggaga | 720 |
| atccgacggg | ttgttactcg | ctcacattta | atgttgatga | aagctggcta | caggaaggcc | 780 |
| agacgcgaat | tatttttgat | ggcgttaact | cggcgtttca | tctgtggtgc | aacgggcgct | 840 |
| gggtcggtta | cggccaggac | agtcgtttgc | cgtctgaatt | tgacctgagc | gcatttttac | 900 |
| gcgccggaga | aaaccgcctc | gcggtgatgg | tgctgcgctg | gagtgacggc | agttatctgg | 960 |
| aagatcagga | tatgtggcgg | atgagcggca | ttttccgtga | cgtctcgttg | ctgcataaac | 1020 |
| cgactacaca | aatcagcgat | ttccatgttg | ccactcgctt | taatgatgat | ttcagccgcg | 1080 |
| ctgtactgga | ggctgaagtt | cagatgtgcg | gcgagttgcg | tgactaccta | cgggtaacag | 1140 |
| tttctttatg | gcagggtgaa | acgcaggtcg | ccagcggcac | cgcgcctttc | ggcggtgaaa | 1200 |
| ttatcgatga | gcgtggtggt | tatgccgatc | gcgtcacact | acgtctgaac | gtcgaaaacc | 1260 |
| cgaaactgtg | gagcgccgaa | atcccgaatc | tctatcgtgc | ggtggttgaa | ctgcacaccg | 1320 |
| ccgacggcac | gctgattgaa | gcagaagcct | gcgatgtcgg | tttccgcgag | gtgcggattg | 1380 |
| aaaatggtct | gctgctgctg | aacgcaagc | cgttgctgat | cgaggcgtt | aaccgtcacg | 1440 |
| agcatcatcc | tctgcatggt | caggtcatgg | atgagcagac | gatggtgcag | gatatcctgc | 1500 |
| tgatgaagca | gaacaacttt | aacgccgtgc | gctgttcgca | ttatccgaac | catccgctgt | 1560 |
| ggtacacgct | gtgcgaccgc | tacggcctgt | atgtggtgga | tgaagccaat | attgaaaccc | 1620 |
| acggcatggt | gccaatgaat | cgtctgaccg | atgatccgcg | ctggctaccg | gcgatgagcg | 1680 |
| aacgcgtaac | gcgaatggtg | cagcgcgatc | gtaatcaccc | gagtgtgatc | atctggtcgc | 1740 |

| | |
|---|---|
| tggggaatga atcaggccac ggcgctaatc acgacgcgct gtatcgctgg atcaaatctg | 1800 |
| tcgatccttc ccgcccggtg cagtatgaag gcggcggagc cgacaccacg gccaccgata | 1860 |
| ttatttgccc gatgtacgcg cgcgtggatg aagaccagcc cttccgggct gtgccgaaat | 1920 |
| ggtccatcaa aaaatggctt tcgctacctg gagagacgcg cccgctgatc ctttgcgaat | 1980 |
| acgcccacgc gatgggtaac agtcttggcg gtttcgctaa atactggcag gcgtttcgtc | 2040 |
| agtatccccg tttacagggc ggcttcgtct gggactgggt ggatcagtcg ctgattaaat | 2100 |
| atgatgaaaa cggcaacccg tggtcggctt acggcggtga ttttggcgat acgccgaacg | 2160 |
| atcgccagtt ctgtatgaac ggtctggtct ttgccgaccg cacgccgcat ccagcgctga | 2220 |
| cggaagcaaa acaccagcag cagttttttcc agttccgttt atccgggcaa accatcgaag | 2280 |
| tgaccagcga atacctgttc cgtcatagcg ataacgagct cctgcactgg atggtggcgc | 2340 |
| tggatggtaa gccgctggca agcggtgaag tgcctctgga tgtcgctcca caaggtaaac | 2400 |
| agttgattga actgcctgaa ctaccgcagc cggagagcgc cgggcaactc tggctcacag | 2460 |
| tacgcgtagt gcaaccgaac gcgaccgcat ggtcagaagc cgggcacatc agcgcctggc | 2520 |
| agcagtggcg tctggcggaa aacctcagtg tgacgctccc cgccgcgtcc cacgccatcc | 2580 |
| cgcatctgac caccagcgaa atggattttt gcatcgagct gggtaataag cgttggcaat | 2640 |
| ttaaccgcca gtcaggcttt ctttcacaga tgtggattgg cgataaaaaa caactgctga | 2700 |
| cgccgctgcg cgatcagttc acccgtgcac cgctggataa cgacattggc gtaagtgaag | 2760 |
| cgacccgcat tgaccctaac gcctgggtcg aacgctggaa ggcggcgggc cattaccagg | 2820 |
| ccgaagcagc gttgttgcag tgcacggcag atacacttgc tgatgcggtg ctgattacga | 2880 |
| ccgctcacgc gtggcagcat caggggaaaa ccttatttat cagccggaaa acctaccgga | 2940 |
| ttgatggtag tggtcaaatg gcgattaccg ttgatgttga agtggcgagc gatacaccgc | 3000 |
| atccggcgcg gattggcctg aactgccagc tggcgcaggt agcagagcgg gtaaactggc | 3060 |
| tcggattagg gccgcaagaa aactatcccg accgccttac tgccgcctgt tttgaccgct | 3120 |
| gggatctgcc attgtcagac atgtataccc cgtacgtctt cccgagcgaa acggtctgc | 3180 |
| gctgcgggac gcgcgaattg aattatggcc cacaccagtg gcgcggcgac ttccagttca | 3240 |
| acatcagccg ctacagtcaa cagcaactga tggaaaccag ccatcgccat ctgctgcacg | 3300 |
| cggaagaagg cacatggctg aatatcgacg gtttccatat ggggattggt ggcgacgact | 3360 |
| cctggagccc gtcagtatcg gcggaattcc agctgagcgc cggtcgctac cattaccagt | 3420 |
| tggtctggtg tcaaaaataa gctt | 3444 |

```
<210> SEQ ID NO 10
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
```

```
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 10
mgngargcnn wnsmnatgga yccncarcan mg                                    32

<210> SEQ ID NO 11
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 11
ggrtcnccna rnswngtncc ngtnccrtg                                        29

<210> SEQ ID NO 12
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(14)
<223> OTHER INFORMATION: n is a, c, g, or t

<400> SEQUENCE: 12
ggwcdachgg haancchaar gg                                               22

<210> SEQ ID NO 13
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (21)..(21)
```

```
<223> OTHER INFORMATION: n is a, c, g, or t

<400> SEQUENCE: 13
ggcakccaty tygccargtc ncckgt                                                26
```